US007071296B2

(12) United States Patent
Druilhe

(10) Patent No.: US 7,071,296 B2
(45) Date of Patent: Jul. 4, 2006

(54) ***PLASMODIUM FALCIPARUM* ANTIGENS INDUCING PROTECTIVE ANTIBODIES**

(75) Inventor: Pierre Druilhe, Paris (FR)

(73) Assignee: Institut Pasteur, Paris (FR)

( * ) Notice: Subject to any disclaimer, the term of this patent is extended or adjusted under 35 U.S.C. 154(b) by 45 days.

(21) Appl. No.: 10/774,602

(22) Filed: Feb. 10, 2004

(65) Prior Publication Data

US 2004/0141987 A1 Jul. 22, 2004

Related U.S. Application Data

(60) Division of application No. 10/294,770, filed on Nov. 15, 2002, now abandoned, which is a continuation-in-part of application No. 10/238,741, filed on Sep. 11, 2002, now Pat. No. 6,949,627, which is a continuation of application No. 09/356,497, filed on Jul. 19, 1999, now Pat. No. 6,472,519, which is a division of application No. 08/416,711, filed as application No. PCT/FR93/01024 on Oct. 18, 1993, now Pat. No. 6,017,538.

(30) Foreign Application Priority Data

Oct. 19, 1992 (FR) .................................. 92 12488

(51) Int. Cl.

| | |
|---|---|
| ***A61K 39/00*** | (2006.01) |
| ***A61K 38/00*** | (2006.01) |
| ***A61K 39/015*** | (2006.01) |
| ***A61K 39/008*** | (2006.01) |
| ***C07K 14/00*** | (2006.01) |
| ***C07K 16/00*** | (2006.01) |
| ***C07K 17/00*** | (2006.01) |

(52) U.S. Cl. ................ 530/300; 424/272.1; 424/184.1; 424/191.1; 424/268.1; 424/265.1; 424/269.1; 530/350; 514/2; 514/12

(58) Field of Classification Search ................ 530/300, 530/350; 424/184.1, 191.1, 268.1, 272.1, 424/269.1, 265.1; 514/21, 2
See application file for complete search history.

(56) References Cited

U.S. PATENT DOCUMENTS

| | | | | |
|---|---|---|---|---|
| 4,835,259 | A | 5/1989 | Reese et al. | |
| 5,589,343 | A * | 12/1996 | Marchand et al. | 435/7.22 |
| 5,599,542 | A * | 2/1997 | Marchand et al. | 424/191.1 |
| 5,602,031 | A * | 2/1997 | Marchand et al. | 435/252.3 |
| 5,690,941 | A * | 11/1997 | Druilhe et al. | 424/272.1 |
| 5,928,901 | A * | 7/1999 | Marchand et al. | 435/69.3 |
| 6,017,538 | A | 1/2000 | Druilhe et al. | |
| 6,100,067 | A * | 8/2000 | Druilhe et al. | 435/69.3 |
| 6,191,270 | B1 | 2/2001 | Druilhe et al. | |
| 6,319,502 | B1 * | 11/2001 | Guerin-Marchand et al. | 424/191.1 |
| 6,472,519 | B1 | 10/2002 | Druilhe et al. | |
| 6,824,816 | B1 * | 11/2004 | Aaltonen et al. | 427/124 |
| 6,942,866 | B1 * | 9/2005 | Birkett | 424/268.1 |
| 6,949,627 | B1 * | 9/2005 | Druilhe et al. | 530/387.1 |
| 2002/0155441 | A1 | 10/2002 | Druilhe et al | |
| 2003/0059436 | A1 | 3/2003 | Chishti et al. | |
| 2003/0104003 | A1 | 6/2003 | James et al. | |
| 2003/0161840 | A1 * | 8/2003 | Druilhe | 424/191.1 |
| 2004/0067236 | A1 * | 4/2004 | Cohen et al. | 424/185.1 |
| 2004/0141987 | A1 * | 7/2004 | Druilhe | 424/184.1 |
| 2005/0004346 | A1 * | 1/2005 | Dziegiel et al. | 530/350 |
| 2005/0075496 | A1 * | 4/2005 | Druilhe et al. | 536/23.7 |
| 2005/0112133 | A1 * | 5/2005 | Druilhe | 424/185.1 |
| 2005/0260224 | A1 * | 11/2005 | Gillespie et al. | 424/191.1 |
| 2005/0266017 | A1 * | 12/2005 | Druilhe et al. | 424/191.1 |

FOREIGN PATENT DOCUMENTS

| | | | |
|---|---|---|---|
| EP | 1201250 | A1 * | 5/2002 |
| GB | 2378949 | A * | 2/2003 |
| WO | WO 88/00595 | | 1/1988 |
| WO | WO 90/02752 | | 3/1990 |
| WO | WO 94/09140 | A1 * | 4/1994 |

OTHER PUBLICATIONS

Oeuvray et al, Blood, 1994, 84/5:1594-1602.*
Huber et al, Molecular and Biochemical Parasitology, 1997, 87:231-234.*
Stowers et al, TRENDS in Parasitology, 2001, 17/9;415-419.*
Ntumngia et al, Molecular and Biochemical Parasitology, 2004, 137:349-353.*
Arevalo-Herrera et al, Molecular Immunology, 2001, 38:443-455.*
Bouharoun-Tayoun et al, Experimental Parasitology, 2004, (Article in Press).*
Black et al, Molecular and Biochemical Parasitology, 2000, 111:447-451.*
Black et al, Molecular and Biochemical Parasitology, 2002, 120:215-224.*
Theisen et al, Vaccine, 2001, 19:204-212.*
Cowman et al, FEBS Letters, 2000, 476:84-88.*

(Continued)

*Primary Examiner*—N. M. Minnifield
(74) *Attorney, Agent, or Firm*—Oblon, Spivak, McClelland, Maier & Neustadt, P.C.

(57) ABSTRACT

The present invention relates to immunogenic compositions comprising as an immunogen a long synthetic or recombinant peptide of a merozoite surface protein 3b (MSP-3b) peptide, an MSP-3c peptide and a MSP-3d peptide. Vaccines against malaria are also disclosed using these peptides alone or in combination with a pharmaceutically acceptable carrier.

1 Claim, 5 Drawing Sheets

OTHER PUBLICATIONS

Galinski et al, Parasitology Today, 1996, 12/1:20-29.*
Cooke et al, Parasitology Today, 2000, 16/5:177-178.*
Galinski et al, 1999, Molecular and Biochemical Parasitology, 1999, 101:131-147.*
Shi et al, PNAS USA, 1999, 96:1615-1620.*
Saul et al, Vaccine, 1999, 17:3145-3159.*
Gordon, Vaccine, 1993, 11/5:591-593 Abstract Only.*
Rafi-Janajreh et al, Experimental Parasitology, 2002, 101:3-12.*
Kurtis et al, Infection and Immunity, 1999, 67/7:3424-3429.*
Kurtis et al, TRENDS in Parasitology, 2001, 17/5:219-223.*
Cox, Nature, 1992, 360:417-418.*
Joshi et al, Infection and Immunity, 2000, 68/1:141-150.*
Soe et al, Infection and Immunity, Jan. 2004, 72/1:247-252.*
Badell et al, J. Exp. Med., 2000, 192/11:1653-1659.*
Carvalho et al, Scandinavian J. Immunology, 2004, 59:363-372.*
Moorthy et al, Lancet, 2004, 363:150-156.*
Ballou et al, Am. J. Trop. Med. Hyg., 2004, 71/Suppl2:239-247.*
Singh et al, J. Infectious Diseases, 2004, 190/5:1010-1018.*
Gardner et al, Nature, 2002, 419:498-511.*
Okenu et al, Molecular and Biochemical Parasitology, 2000, 109:185-188.*
Oeuvray et al, Mem. Inst. Oswaldo Cruz, Rio de Janeiro, 1994, 89/Suppl. II:77-80.*
McColl et al, Molecular and Biochemical Parasitology, 1994, 68:53-67.*
U.S. Appl. No. 10/774,602, filed Feb. 10, 2004, Druilhe.
Bouharoun-Tayoun et al, Infection and Immunity, 1992, 60/4:1473-1481.
Li et al, Parasitology, 1987, 95:229-240.
Druilhe et al, Infection and Immunity, 1987, 55/4:888-891.
Khusmith et al, Transactions of the Royal Society of Tropical Medicine and Hygiene, 1982, 76/3:423-424.
Oeuvray et al, C. R. Acad. Sci. Paris, Sciences de la vie/Life Sciences, 1993, 316:395-399.
McColl et al, Molecular and Biochemical Parasitology, 1997, 90:21-31.
Badell et al, J. Exp. Medicine, 2000, 192/11:1653-1659.
Druilhe et al, Annals of Tropical Medicine and Parasitology, 1997, 91/Suppl. 1:S37-S53.
Gruner et al, Trends in Parasitology, Feb. 2003, 19/2:74-78.
Carvalho et al, Mem. inst. Oswaldo Cruz, Rio de Janeiro, Nov. 1999/Suppl. II:216.
Carvalho et al, Mem. Inst. Oswaldo Cruz, Rio de Janeiro, Nov. 1998, 93/Suppl. II:263-264.

* cited by examiner

SEQUENCE LISTING

<160> NUMBER OF SEQ ID NOS: 14

<210> SEQ ID NO 1

-continued

<211> LENGTH: 64
<212> TYPE: PRT
<213> ORGANISM: Plasmodium falciparum

<400> SEQUENCE: 1

His Glu Arg Ala Lys Asn Ala Tyr Gln Lys Ala Asn Gln Ala Val Leu
1 5 10 15

Lys Ala Lys Glu Ala Ser Ser Tyr Asp Tyr Ile Leu Gly Trp Glu Phe
20 25 30

Gly Gly Gly Val Pro Glu His Lys Lys Glu Glu Asn Met Leu Ser His
35 40 45

Leu Tyr Val Ser Ser Lys Asp Lys Glu Asn Ile Ser Lys Glu Asn Glu
50 55 60

<210> SEQ ID NO 2
<211> LENGTH: 23
<212> TYPE: PRT
<213> ORGANISM: Plasmodium falciparum

<400> SEQUENCE: 2

His Glu Arg Ala Lys Asn Ala Tyr Gln Lys Ala Asn Gln Ala Val Leu
1 5 10 15

Lys Glu Ala Ser Ser Tyr Asp
20

<210> SEQ ID NO 3
<211> LENGTH: 27
<212> TYPE: PRT
<213> ORGANISM: Plasmodium falciparum

<400> SEQUENCE: 3

Ala Lys Glu Ala Ser Ser Tyr Asp Tyr Ile Leu Gly Trp Glu Phe Gly
1 5 10 15

Gly Gly Val Pro Glu His Lys Lys Glu Glu Asn
20 25

<210> SEQ ID NO 4
<211> LENGTH: 28
<212> TYPE: PRT
<213> ORGANISM: Plasmodium falciparum

<400> SEQUENCE: 4

Pro Glu His Lys Lys Glu Glu Asn Met Leu Ser His Leu Tyr Val Ser
1 5 10 15

Ser Lys Asp Lys Glu Asn Ile Ser Lys Glu Asn Glu
20 25

<210> SEQ ID NO 5
<211> LENGTH: 192
<212> TYPE: DNA
<213> ORGANISM: Plasmodium falciparum

<400> SEQUENCE: 5
catgaaaggg caaaaaatgc ttatcaaaaa gcaaaccaag ctgttttaaa agcaaaagaa 60
gcttctagtt atgattatat tttaggttgg gaatttggag gaggcgttcc agaacacaaa 120
aaagaagaaa atatgttatc acatttatat gtttcttcaa aggataagga aaatatatct 180
aaggaaaatg ag 192

<210> SEQ ID NO 6
<211> LENGTH: 75

-continued

```
<212> TYPE: DNA
<213> ORGANISM: Plasmodium falciparum

<400> SEQUENCE: 6

catgaaaggg caaaaaatgc ttatcaaaaa gcaaaccaag ctgttttaaa agcaaaagaa     60

gcttctagtt atgat                                                      75


<210> SEQ ID NO 7
<211> LENGTH: 81
<212> TYPE: DNA
<213> ORGANISM: Plasmodium falciparum

<400> SEQUENCE: 7

gcaaaagaag cttctagtta tgattatatt ttaggttggg aatttggagg aggcgttcca     60

gaacacaaaa aagaagaaaa t                                               81


<210> SEQ ID NO 8
<211> LENGTH: 84
<212> TYPE: DNA
<213> ORGANISM: Plasmodium falciparum

<400> SEQUENCE: 8

ccagaacaca aaaaagaaga aaatatgtta tcacatttat atgtttcttc aaaggataag     60

gaaaatatat ctaaggaaaa tgag                                            84


<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9

gaaagggcaa aaaatgctta t                                               21


<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10

taaaaggaat ctatataaaa g                                               21


<210> SEQ ID NO 11
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 11

Tyr Glu Lys Ala Lys Asn Ala Tyr Gln Lys Ala Asn Gln Ala Val Leu
1               5                   10                  15

Lys Ala Lys Glu Ala Ser Ser Tyr Asp
            20                  25


<210> SEQ ID NO 12
<211> LENGTH: 27
<212> TYPE: PRT
<213> ORGANISM: Artificial Sequence
<220> FEATURE:
```

-continued

```
<223> OTHER INFORMATION: Synthetic Peptide

<400> SEQUENCE: 12

Ala Lys Glu Ala Ser Ser Tyr Asp Tyr Ile Leu Gly Trp Glu Phe Gly
1               5                   10                  15

Gly Gly Val Pro Glu His Lys Lys Glu Glu Asn
            20                  25


<210> SEQ ID NO 13
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 13

Pro Glu His Lys Lys Glu Glu Asn Met Leu Ser His Leu Tyr Val Ser
1               5                   10                  15

Ser Lys Asp Lys Glu Asn Ile Ser Lys Glu Asn Asp
            20                  25


<210> SEQ ID NO 14
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 14

Met Leu Ser His Leu Tyr Val Ser Ser Lys Asp Lys Glu Asn Ile Ser
1               5                   10                  15

Lys Glu Asn Asp Asp Val Leu Asp Glu Lys Glu Glu Glu Ala Glu Glu
            20                  25                  30

Thr Glu Glu Glu Glu Leu Glu Glu Lys
        35                  40
```

*PLASMODIUM FALCIPARUM* ANTIGENS INDUCING PROTECTIVE ANTIBODIES

The present invention is a divisional of U.S. patent application Ser. No. 10/294,770 filed on Nov. 15, 2002, now abandoned. which is a continuation in part of U.S. application Ser. No. 10/238,741 filed Sep. 11, 2002, now U.S. Pat. No. 6,949,627, which is a continuation of application Ser. No. 09/356,497 filed Jul. 19, 1999, now U.S. Pat. No. 6,472,519, which is a divisional of U.S. application Ser. No. 08/416,711, filed Aug. 8, 1995, now U.S. Pat. No. 6,017,538, which was originally filed as International Application no. PCT/FR93/01024 on Oct. 18, 1993.

BACKGROUND OF THE INVENTION

The object of the present invention is novel preparations for a broad-spectrum antiplasmodial vaccine.

The object of the invention is also a vaccinating antigen of *Plasmodium falciparum* capable of inducing a resistance to the parasite which reproduces that observed in the mechanism of protective immunity or premunition.

The object of the invention is also preparations of monoclonal or polyclonal antibodies or chimeric fragments obtained from these antibodies specific for these antigens and likely to form part of a composition for passive immunotherapy.

The object of the present invention is also a kit permitting the in vitro diagnosis of the infection of an individual by a broad spectrum of plasmodial strains.

In another aspect, the present invention relates to an immunogenic composition comprising a long synthetic peptide comprising the epitopes contained within the merozoite surface protein-3b (MSP-3b) peptide, MSP-3c peptide and MSP-3d peptide.

A vaccine against malaria is also disclosed comprising the epitopes contained within the merozoite surface protein-3b (MSP-3b) peptide, MSP-3c peptide and MSP-3d peptide and a pharmaceutically acceptable carrier such as Alum and/or Montanide.

A method of the in vitro detection of a premunition state against malaria, as well as other methods for treating cerebral malaria and lowering parasitemia are also encompassed by the present invention.

The parasites responsible for malaria in man, including in particular, *Plasmodium falciparum* or *Plasmodium vivax* to mention only the principal ones, exhibit different morphologies in the human host and express different antigens as a function of their localization in the organism of the infected host. The morphological and antigenic differences of these parasites during their life cycle in man enable at least four distinct stages of development to be defined.

The very first stage of development of the parasite in man corresponds to the sporozoite form introduced into the blood of the host by bites of insect vectors of the parasite. The second stage corresponds to the passage of the parasite into the liver and to the infection of the hepatic cells in which the parasites develop to form the hepatic schizonts which, when they are mature (for example, in the case of *P. falciparum* on the $6^{th}$ day after penetration of the sporozoites) release hepatic merozoites by bursting. The third stage is characterized by the infection of the blood erythrocytes by the asexual forms (merozoites) of the parasite; this erythrocytic stage of development corresponds to the pathogenic phase of the disease. The fourth stage corresponds to the formation of the forms with sexual potential (or gametocytes), which will become extracellular sexual forms—or gametes—in the mosquito.

It is known that very many studies have been undertaken to isolate from strains of parasites which infect a human host polypeptide fractions to permit the in vitro diagnosis of malaria by the detection of corresponding antibodies, on the one hand, and to attempt to vaccinate against malaria, on the other.

In 1976 the maintenance (so long-waited) of *P. falciparum* in continuous culture in human RBC was accomplished (Trager and Jensen, Science 1976, 193:673; Haynes et al., 1976). This achievement facilitated access to the parasite considerably and stimulated research, which since then has experienced a rapid development. Efforts have been oriented mainly towards the development of a vaccine which in the future will be necessary to control malaria, whose incidence is becoming worse in as much as resistance of the parasite to drugs is spreading in different parts of the world.

In the search for a vaccine against the agent responsible for malaria, biologists are confronted with various problems not observed with other infectious agents such as viruses or bacteria. Of these special difficulties with the parasite it should be mentioned principally:

The complexity of the biological cycle of the plasmodium taking place in two different hosts, the mosquito and man, undergoing sexual reproduction in the one and 2 different phases of asexual reproduction in the other. Thus, 2 stages take place in man differing in their site of development (the liver and blood circulation) and in their antigenic specificities.

The antigenic diversity of the parasite. Since 1983 the plasmodial antigens have been cloned and their nucleotide and protein sequences have been analyzed. This detailed study shows that more than 50% of the known antigens exhibit a high degree of polymorphism from one strain to another.

At the immunological level, the host-parasite relationship is very subtle. As has already been mentioned, for a given parasite it is very different depending on the host in which it evolves. This leads to the difficulty of interpretation of the results obtained in the experimental models.

Furthermore, the natural infection sterilizing immunity is never seen like that observed, for example, in viruses. However, there is no doubt that an acquired immunity exists but it is partial and labile.

Thus the complexity and the diversity of the parasite as well as the unusual nature of the immune response that it elicits are the major reasons for the absence of an antimalarial vaccine at present.

The research approach most often taken in the development of a vaccine against malaria due to *P. falciparum* hence consists of the identification (on the basis of the information cited above) of a potential candidate, and then the evaluation of its value either in vitro by testing specific antibodies in the inhibition of the growth of the parasite or of certain of its properties (cytoadhesion, rosette formation . . . ) or in vivo by the immunization of monkeys often with the complete Freund adjuvant. The present situation may thus be summed up as the existence of a large number of potential candidates characterized by their biochemical properties, their nucleotide and protein sequences, their degree of polymorphism, their localization on the parasite etc. Nevertheless, the researchers dispose of limited means for assessing the value of their candidates: 1) in vitro tests implicating mechanisms of action of antibodies whose validity in vivo is poorly documented, 2) vaccinations of non-human primates, and hence the evaluation of the effect of a vaccine on an experimental infection is based on parasitological and clinical parameters and particularly the type of immunity which may be induced which are different from those of the natural infection in man.

The strict specificity of the host-parasite relationship leads under natural conditions to the opposite of what is observed in the animal models, to an equilibrium in which the parasite survives by inducing in its natural host a non-sterilizing immunity. The chronic nature of the parasitic infection suggests that the majority of the molecular components of the parasitic infection are selected so as to protect the microorganism against the immune defenses of the individual infected, and do so by means of escape which are varied but specifically adapted to the natural host. In the experimental host, the poorly adapted parasite defends itself less well against the immune system and protection against a single treated infection is easy to obtain, and vaccination is still easier to obtain.

Gordon-Thomson, Immunity in Malaria, Trans. Roy. Soc. Trop. Med. Hyg. XXVI (6) 483–514) clearly concluded that immunity against *P. falciparum* can only be acquired in the regions where transmission is essentially continuous year after year. This “tolerance” to parasitism requires at the individual level an uninterrupted infection for about 15 years, sometimes 20 years and up to 26 years in a study conducted in Panama. An immunity associated with a latent infection necessary for the maintenance of the protection results from this. Sergent (1935) suggested the term “premunition” to define this “particular state of resistance contemporaneous with the infection and ceasing with it.”

Thus, the immunity (or premonition) against *P. falciparum* acquired by man in a holo- or hyperendemic zone is characterized by:

- a very long delay prior to its installation (15 to 20 years of infection);
- its incapacity to abolish the infection, it is a non-sterilizing immunity; and
- its liability. In the absence of any reinfection (during more than one year), the premunition is lost and the subject again becomes susceptible to the disease if subject to a new infection.

The indications in favour of humoral immunity in acquired protection against malaria come from the first attempts at passive transfer of serum from an individual in the “chronic” phase who had reached a state of premunition (i.e., showing circulating parasites in small numbers without any clinical manifestation) to a subject in the acute phase. The condition of this latter is found to be improved subsequent to this passive transfer (Sotiriades 1917, Attempts at serotherapy in malaria Greek Med. XIX: 27–28).

The role of antibodies in premunition is demonstrated by several experiments of passive transfer carried out at the beginning of the 1960s. The transfer of IgG purified from hyperimmune African adult serum cures child victims of an acute infection by appreciably reducing their parasitemia (Cohen et al., 1971, Trans. Roy. Soc. Trop. Med. Hyg. 65(2): 125–135; McGregor et al., 1964, the passive transfer of human material immunity, Am. J. Trop. Med. Hyg. 13: 237–239). The newborn are protected up to the third month of their life as a result of maternal antibodies; this is proved by the beneficial effect of the IgG of the umbilical cord transferred to children suffering from an acute attack due to *P. falciparum* (Edozien et al., 1962).

The development of immunity and its efficacy in the protection of man against *P. falciparum* nonetheless proves the existence of parasite molecules which are the targets of an effective immune defense.

Recent experiments have made it possible to show that a) the G immunoglobulins (IgG) of immune African adults are protective by passive transfer in man infected with malaria (Sabchareon et al., Amer. J. of Trop. Med. and Hyg., vol. 45, No. 3, September 1991, 297–308), b) that, contrary to what is believed to be established, these antibodies are incapable of directly inhibiting the invasion of red cells by the parasites; on the other hand, they act by an antibody-dependent cellular inhibition mechanism (ADCI) in which the monocyte plays the role of effector cell (Bouharoun-Tayoun et al., J. Exp. Med., vol. 172, December 1990, pp. 1633–1641; S. Khusmith et al., 1983, Inf. Imm. 41(1): 219 and F. Lunel et al., 1989 Inf. Imm. 57: 2043), c) This mechanism necessarily implicates cytophilic antibodies, i.e., those capable of binding to the monocyte through their Fc receptor. In fact, there has been observed in the serum of protected subjects a prevalence of cytophilic isotypes IgG1 and IgG3 and in non-protected subjects a preponderance of non-cytophilic classes, IgG2 and/or IgM (H. Bouharoun-Tayoun et al., 1992, Infection and Immunity, pp. 1473–1481).

SUMMARY OF THE INVENTION

One of the objectives of the present invention is the development of polypeptides for the vaccination of humans against malaria, polypeptides which are a target of the defense mechanisms prevailing in the individuals having acquired an immunity by prolonged exposure to the parasite and their use in a vaccine, by attempting to reproduce the same state of resistance by the same mechanism as that observed in the establishment of protective immunity.

The object of the invention is also the use of these same polypeptides in an in vitro diagnostic kit for the infection in man by a broad spectrum of plasmodial strains.

In another aspect, the present invention provides an immunogenic composition comprising a long synthetic peptide comprising the epitopes contained within the merozoite surface protein-3b (MSP-3b) peptide, MSP-3c peptide and MSP-3d peptide.

A vaccine against malaria is also provided comprising the epitopes contained within the merozoite surface protein-3b (MSP-3b) peptide, MSP-3c peptide and MSP-3d peptide and a pharmaceutically acceptable carrier such as Alum and/or Montanide.

A method of the in vitro detection of a premunition state against malaria, as well as other methods for treating cerebral malaria and lowering parasitemia, are also encompassed by the present invention.

PREFERRED EMBODIMENTS OF THE INVENTION

Figure 1:
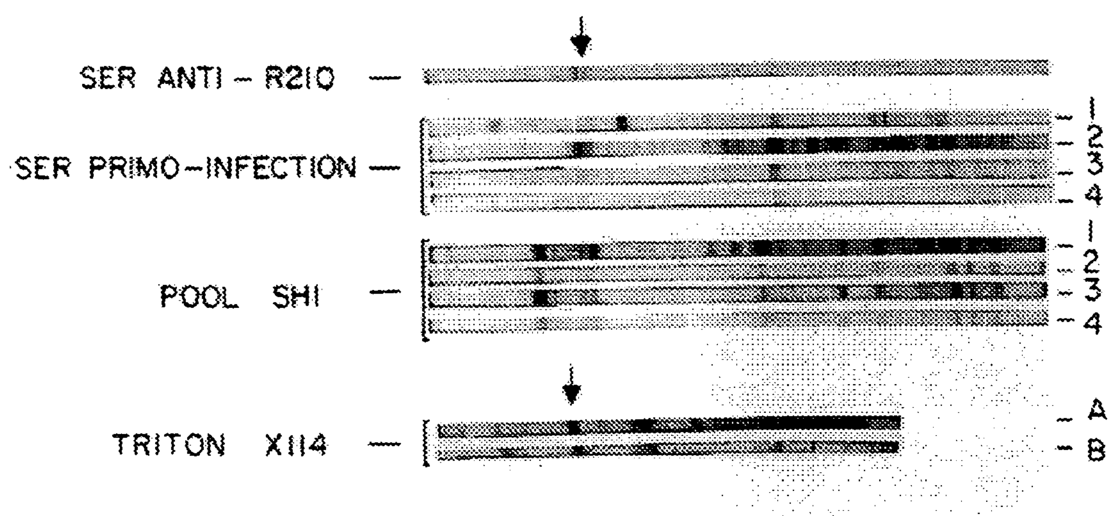
FIG. 1 shows the detection of the parasite protein of 48,000 (indicated by the arrows) by immunoblot. The reactivity of the serum of mice immunized with DG210 is studied in immunotransfer on the antigens of the blood stages of *P. falciparum* extracted into SDS (anti-R210 ser) or into Triton-X114 detergent phase (A) and aqueous phase (B). The reactivity of the human sera is studied on the SDS extracts by revealing the isotypes IgG12 (1), IgG2 (2), IgG3 (3) and IgG4 (4). HIS: hyperimmune serum.

By the term "LSP" is meant a long synthetic peptide. This peptide comprises the epitopes contained within MSP-3b and/or MSP-3c and/or MSP-3d.

By "MSP-3" is meant the merozoite surface protein 3.

By "native MSP-3 protein" is meant that the protein can be purified in its natural state or it can be reproduced recombinantly by methods known in the art. Such a "native MSP-3 protein" has the same immunological properties as the natural MSP-3 protein.

Other terms may be further defined later in the text.

Montanide adjuvants are a group of oil/surfactant based adjuvants in which different surfactants are combined with either a non-metabolizable mineral oil, a metabolizable oil or a mixture of the two. They are prepared for use as an emulsion with an aqueous Ag solution and are available from Seppic, Paris, France.

The invention relates more particularly to molecules or peptide or polypeptide compositions characterized by the presence in their structure of one or more peptide sequences bearing one or more epitopes characteristic of a protein recognized by antibodies of the cytophilic class, i.e. capable of binding to the FcR receptors of the monocytes through their Fc region, and not recognized by non-cytophilic antibodies and of promoting an antibody-dependent cytotoxicity mechanism (ADCI).

A protein of the invention is a merozoite surface protein of 48,000 molecular weight (48 kD), exhibiting the properties given below.

The polypeptides of the invention were obtained by

- the identification of a part of this protein of 48,000 daltons molecular weight (48 kD) of the merozoite surface, this identification being described below,
- the biochemical and immunological characterization of the 48 kD protein,
- the screening of a genomic library of the plasmodium for its capacity to inhibit the coupling of a specific monoclonal antibody of the IgM type which has the special characteristic of blocking the ADCI-type reaction ("antibody-dependent cellular inhibition") induced by the specific IgG of the plasma of the subjects protected by premonition,
- the characterization of the proteins synthesized by the clones selected,
- the sequencing of the insert of the clone selected,
- the search for the functional effect of the antibodies corresponding to this protein in the tests described.

The value of the proteins and peptides of the invention and the strategy used to obtain them are made explicit in the description below.

Selection Strategy for the Proteins and Peptides

1—In *Infection and Immunity* (pp 1473–1481, April 1992), the authors study the isotypic distribution of individuals infected by the plasmodium exhibiting various immunological states. In this way they have shown that the unprotected subjects have an anti-plasmodial plasma antibody composition very much in favour of the non-cytophilic isotypes, namely IgG2 and IgM. In certain cases, this equilibrium relates to the antibodies against all of the malarial polypeptides detectable by Western blot (procedure described in Molecular Cloning, 1989, Sambrook et al.) whereas in other cases it was possible to demonstrate IgG2 specific for a given polypeptide, often a polypeptide of 48 kD appearing in certain isolates in the form of a dimer or a polypeptide of 80–100 kD. On the other hand, the polypeptide of 48 kD is always recognized by the cytophilic isotypes IgG1 and IgG3 in adults who have acquired resistance to the disease, or a state of premunition.

2—It has often been observed in competition experiments that the total purified Ig of unprotected individuals block the ADCI reaction (see description below) induced by the IgG of resistant subjects. This result suggests that the unprotected subjects have developed antibodies directed against the same epitopes as those which are recognized by the protecting antibodies, but owing to the non-cytophilic character of the IgG2 or IgM derived from the unprotected subjects, these antibodies are incapable of promoting the destructive effect of the monocytes but, on the other hand, are capable of entering into competition with antibodies effective in ADCI. When such a competitive effect was identified by using human sera in which the antibodies against the 48 kD protein were predominantly of the IgG2 isotype, that clearly demonstrates the significance of this 48 kD protein.

The ADCI test has already been described in the publication cited above (H. Bouharoun-Tayoun et al., Khusmith et al., Lunel et al.). Briefly, it is a test of the inhibition of growth of the parasite by the IgG in the presence of monocytes. The monocytes are isolated by adhesion to the plastic (in a 96-wells plate) from the fraction of mononucleated cells of the peripheral blood of a normal donor. A synchronous culture of *P. falciparum* at 0.5% parasitemia in mature form is added to the monocytes in a monocytes/red cells ratio of about 1/200. The hematocrit being 2%, the medium is supplemented by the serum or the IgG to be tested. The reference cultures consist of parasites in the presence of normal IgG, parasites in the presence of monocytes and normal IgG, parasites in the presence of the IgG to be tested.

Depending on the case, the culture will be stopped after 24, 48, 72 or 96 hours. In the last two cases, 50 microliters of the culture medium are added. The final parasitemia in each of the wells is estimated by counting 10,000 red cells on stained smears. The results are presented in the form of a specific growth inhibition index (SI) expressed as a percentage and calculated as follows, taking into consider ation of the possible inhibitory effect on the monocyte culture and/or antibodies alone:

$$SI = 1 - \frac{\%\ \text{parasitemia culture} + \text{IgG test} / \%\ \text{parasitemia monocytes} + \text{IgG test}}{\%\ \text{parasitemia monocytes} + \text{IgG} / \%\ \text{parasitemia culture} + \text{IgG}}$$

This selection strategy for a potentially vaccinating protein of 48 kD according to the recognition criteria by cytophilic antibodies in protected subjects and non-cytophilic antibodies in unprotected subjects as well as by their capacity to induce antibodies capable of cooperating with monocytes in ADCI have led to the selection of this 48 kD protein or peptides representing the epitopic regions of this protein as potentially very useful candidates for inducing the protective immunological effect against infections of *P. falciparum* in patients.

The invention also relates particularly to molecules or peptide or polypeptide compositions characterized by the presence in their structure of one or more peptide sequences bearing one or more epitopes characteristic of the protein and meeting the three criteria:

- recognition by antibodies of the cytophilic class in protected subjects and non-cytophilic in unprotected subjects,
- their capacity to induce antibodies capable of cooperating with monocytes in ADCI,
- their slight or non-existent polymorphic character in as much as the protective immunity can be exercised with respect to a large number of strains.

The molecules of the invention are all of the molecules bearing epitopes, recognized by antibodies recognizing epitopes borne by the 48 kD protein of the merozoite surface.

A polypeptide composition according to the invention is characterized by the presence of a sequence of 64 amino acids or a derivative sequence possessing the same antigenic properties, and an example of which is given in the following formula I (SEQ ID NO.1):

```
his glu arg ala lys asn ala tyr gln lys
ala asn gln ala val leu lys ala lys glu
ala ser ser tyr asp tyr ile leu gly trp
glu phe gly gly gly val pro glu his lys
lys glu glu asn met leu ser his leu tyr
val ser ser lys asp lys glu asn ile ser
lys glu asn glu
```

The invention relates primarily to synthetic monomeric peptides comprising a unique peptide sequence of 64 amino acids corresponding respectively to the formula indicated above and whose terminal amino acids possess free amino and carboxylic extremities respectively, or oligomers containing in particular multiples of any one of the above-mentioned peptide sequence.

The invention also relates to a purified polypeptide selected in the group comprising the following peptides:

```
MSP3a: YEKAKNAYQKANQAVLKAKEASSYD,               (SEQ ID No: 11)
MSP3b: AKEASSYDYILGWEFGGGVPEHKKEEN,             (SEQ ID No: 12)
MSP3c: PEHKKEENMLSHLYVSSKDKENISKEND,            (SEQ ID No: 13)
MSP3d: MLSHLYVSSKDKENISKENDDVLDEKEEEAEETEEEELEEK, (SEQ ID No: 14)
and
```

combinations thereof.

Another aspect of the invention is a long synthetic or recombinant polypeptide comprising epitopes contained within MSP-3a and/or MSP-3b and/or MSP-3c peptide and/or MSP-3d peptides, wherein said long synthetic or recombinant polypeptide comprises at least 26, at least 27, or at least 40 amino acids.

A long synthetic or recombinant polypeptide comprising epitopes contained within MSP-3a and/or MSP-3b and/or MSP-3c peptide and/or MSP-3d peptides, and comprising more than 90 amino acids, is also part of the present invention. In such a long peptide, any amino acid not present in MSP-3a, MSP-3b, MSP-3c and MSP-3d sequences can be added, either between the different conformational epitopes or at the extremities of the peptide, provided it does not prevent said conformational epitopes from being accessible.

It is obvious that the free reactive functions which some amino acids forming part of the constitution of the molecules according to the invention are likely to possess, in particular the free carboxyl groups borne by the Glu residues and by the C-terminal amino acid, on the one hand, and/or the free groups borne by the N-terminal amino acid or by amino acids in the interior of the peptide chain, for example Lys, on the other, may be modified provided that this modification does not lead to a modification of the antigenic, possibly immunogenic properties, of the entire molecule. The molecules thus modified are naturally included in the framework of the protection given to the invention by the claims. These carboxylic functions are possibly acylated or esterified.

Other modifications are also included in the framework of the invention. In particular, amine or ester functions, or both at once, of the terminal amino acids may themselves be engaged in linkages with other amino acids. For example, the N-terminal amino acid may be linked to a sequence comprising one or more amino acids corresponding to a part of the C-terminal region of another peptide conforming to the definition which has been given to it above, or vice versa.

It will be obvious that any peptide sequence derived from the modification of the peptide sequence of 64 amino acids by substitution and/or by addition and/or deletion of one or more amino acids is included in the framework of the protection given to the invention by the Claims, provided that this modification does not impair the antigenic or immunogenic properties of the polypeptide, in particular when these immunogenic properties have been reinforced adequately, for example by combination of this polypeptide with a suitable immunological adjuvant (for example, a muramylpeptide) or by coupling with a carrier molecule of higher molecular weight (for example a serum albumin or a polylysine) or a toxin of the tetanic type or another antigen of *P. falciparum.*

The invention relates more generally to any molecule characterized by the presence in its structure of one or more peptide sequences exhibiting immunological cross-reactions with the peptide sequence corresponding to the preceding formula with respect to the antibodies inducible by these latter in vivo.

The invention also relates to any peptide whose structure is derived from the preceding one and in particular to one of the three peptides of formula II, III, IV (SEQ ID Nos.2–4)

```
his glu arg ala lys asn ala tyr gln lys ala asn  II
gln ala val leu lys glu ala ser ser tyr asp

ala lys glu ala ser ser tyr asp tyr ile leu gly  III
trp glu phe gly gly gly val pro glu his lys lys
glu glu asn

pro glu his lys lys glu glu asn met leu ser his  IV
leu tyr val ser ser lys asp lys glu asn ile ser
lys glu asn glu
```

As in the case of the first peptide defined above, the different peptides which have just been named may be modified without being excluded from the framework of the invention provided that these structural modificdations do not lead to major changes in their antigenic properties.

The peptides according to the invention may be prepared by the standard procedures used in the field of peptide synthesis. This synthesis may be carried out in homogeneous solution or on a solid phase.

For example, recourse may be had to the procedure of synthesis in a homogeneous solution described by HOUBENWEYL in the monograph entitled "Methoden der Organischen Chemie" (Methods in Organic Chemistry) edited by E. Wunsch, vol. 15-I and II, THIEME, Stuttgart 1974.

This method of synthesis consists of successively condensing in the required order the successive amino acids or of condensing peptide fragments previously formed already containing several amino acids in the required order, it being understood that care will be taken to protect temporarily all of the reactive functions born by these amino acids or peptide fragments, with the exception of those amino and carboxyl functions which are necessarily implicated in the formation of the peptide bonds, in particular after activation of the said carboxyl functions, according to the methods well-known in peptide synthesis. As an alternative, it is possible to have recourse to coupling reactions involving standard coupling reagents of the carbodiimide type, such as for example 1-ethyl-3-(3-dimethyl-amino-propyl)-carbodiimide.

When the aminoacyl residue to be coupled possesses an additional acidic function (in particular, in the case of glutamic acid), these functions are protected, for example, by means of t-butyl ester groups.

In the case of stepwise synthesis, amino acid by amino acid, the synthesis starts preferably by the condensation to the C-terminal amino acid of the next amino acid in the desired sequence and so on, one at a time, the other amino acids selected in appropriate sequence, the synthesis being completed with the attachment of the N-terminal amino acid. According to another preferred procedure of the invention recourse is had to the procedure described by R. D. MERRIFIELD in the article entitled "Solid phase peptide synthesis" (J. Am. Soc., 45: 2149–2154).

In order to synthesize a peptide chain according to the MERRIFIELD procedure, the first amino acid, the C-terminal amino acid of the chain, is attached to a very porous resin polymer. This amino acid is bound to the resin through the intermediary of its carboxyl group and its amino function is protected, for example, by the t-butoxycarbonyl group.

When the first, C-terminal amino acid has thus been attached to the resin, the protecting group of the amino function is removed by washing the resin with acid.

In the case in which the protecting group of the amine function is the t-butoxycarbonyl group, it may be removed by treatment of the resin with trifluoroacetic acid.

The second amino acid is then coupled to the deprotected amine function of the first C-terminal amino acid to furnish the second aminoacyl residue of the desired sequence, counting from the C-terminus. Preferably, the carboxyl function of this second amino acid is activated, for example, by means of dicyclohexylcarbodiimide and the amine function is protected, for example, by means of the t-butoxycarbonyl group.

The first part of the desired peptide chain is thus obtained, which contains two amino acids and the terminal amino function of which is protected. As previously, the amine function is deprotected and it is then possible to proceed to the attachment of the third aminoacyl residue under conditions analogous to those for the addition of the second, penultimate C-terminal amino acid.

In this way, the amino acids which will constitute the peptide chain are added one after the other to the previously deprotected amine group of the portion of the peptide chain already formed which is attached to the resin.

When the desired peptide chain has been assembled in its entirety, the protecting groups of the different side chains of the amino acids constituting the peptide chain are removed and the peptide is cleaved from the resin, for example, with the aid of hydrogen fluoride.

The invention also relates to water-soluble oligomers of the monomeric peptides indicated above.

The oligomerization may cause an increase in the immunogenicity of the monomeric peptides according to the invention. Without such numerical values being considered as limiting, it should nonetheless be mentioned that these oligomers may contain, for example, from 2 to 10 monomeric units.

The monomeric units forming part of this oligomer are either constituted by the polypeptide of sequence I or by the polypeptides of sequence II, III or IV.

In order to carry out the oligomerization, recourse may be had to any polymerization procedure currently used in the field of peptides, this polymerization being conducted until an oligomer or polymer is obtained which contains the required number of monomeric motifs for the acquisition of the desired immunogenicity.

One method of oligomerization or polymerization of the monomer consists in the reaction of the latter with a cross-linking agent such as glutaraldehyde.

It is also possible to have recourse to other methods of oligomerization or coupling, for example to that making use of the successive coupling of monomeric units through the intermediary of their terminal carboxyl and amino functions in the presence of homo- or hetero-bifunctional coupling agents.

For the production of molecules containing one or more motifs of 64 amino acids such as defined above, it is also possible to have recourse to genetic engineering procedures making use of micro-organisms transformed by a specific nucleic acid comprising corresponding suitable nucleotide sequences.

Consequently, the invention also relates to nucleic acids containing one or more of these sequences each comprising 64 triplets of the type indicated above.

The invention also relates to the conjugates obtained by covalent coupling of the peptides according to the invention (or the above-mentioned oligomers) to carrier molecules (natural or synthetic), physiologically acceptable and non-toxic, through the intermediary or complementary reactive groups born respectively by the carrier molecule and the peptide. Examples of suitable groups are illustrated as follows:

As examples of carrier molecules or macromolecular supports forming part of the composition of the conjugates according to the invention, mention should be made of naturally occurring proteins such as tetanus toxoid, ovalbumin, serum albumin, hemocyanins.

Mention should be made, for example, of polylysines or poly (D-L-alanine)-poly (L-lysine) as examples of synthetic macromolecular supports.

The literature mentions other types of macromolecular supports which can be used and which usually have a molecular weight higher than 20,000.

In order to synthesize the conjugates according to the invention, recourse may be had to known procedures such as that described by FRANTZ and ROBERTSON in Infect. and Immunity, 33, 193–198 (1981) or that described in Applied and Environmental Microbiology, (October 1981), vol. 42, No. 4, 611–614 by P. E. KAUFFMAN by using the peptide and the appropriate carrier molecule.

In practice, the following compounds, cited in a non-limiting manner, are advantageously use as coupling agents: glutaraldehyde, ethyl chloroformate, water-soluble carbodiimides: N-ethyl-N' (3-dimethylamino-propyl) carbodiimide HCl, diisocyanates, bis-diazobenzidine, di- and trichloro-s-triazines, cyanogen bromide as well as the coupling agents mentioned in Scand. J. Immunol., (1978), vol. 8, p. 7–23 (AVRAMEAS, TERNYNCK, GUESDON).

It is possible to have recourse to any coupling procedure implicating, on the one hand, one or more reactive functions of the peptide and, on the other, one or more reactive functions of the molecular supports. Advantageously, these are carboxyl and amine functions which can give rise to a coupling reaction in the presence of a coupling agent of the type used in the synthesis of proteins, for example, 1-ethyl-3(3-dimethylamino-propyl)-carbodiimide, N-hydroxybenzotriazole, etc. . . . It is also possible to have recourse to glutaraldehyde, in particular, when it is required to link together amino groups born by the peptide and the molecular support, respectively.

A group of preferred molecules according to the invention is constituted of those possessing an alpha helical conformation, this latter reinforcing the antigenic and immunogenic properties of said molecules. Such molecules possessing an alpha helical conformation were demonstrated by circular dichroism in trifluoroethanol or in aqueous solution.

The molecules according to the invention possess antigenic properties characteristic of the 48 kD antigen of the merozoite specific for the erythrocyte stage of the development of *P. falciparum* and exhibiting the particular characteristics described above.

In fact, as will be more particularly described with the aid of examples of molecules according to the invention in the detailed description which follows, the molecules according to the invention react specifically with the anti-48 kD protein antibodies predominantly of the IgG2 or IgM isotype in the patients sensitive to the infection, and predominantly of the IgG1 or IgG3 isotype in protected subjects.

These molecules according to the invention are capable of triggering in vivo the synthesis of specific immunoglobulins, and are capable of inducing in vivo the neutralization of the merozoite present in the blood, its process in the monocytes and the inactivation of the intraerythocytic development of *P. falciparum* subsequent to an interaction between the monocytes and the extra-erythrocytic free parasites or merozoites through the intermediary of a cytophilic antibody by binding of the Fc fragment of the immunoglobulin to the gamma receptor of the monocyte.

In another aspect the present invention relates to an immunogenic composition comprising as an immunogen a long synthetic peptide comprising the epitopes contained within a MSP-3a peptide, a MSP3b peptide, a MSP-3c peptide or a MSP-3d peptide, as well as combinations of these epitopes.

In the following definition of MSP-3a, MSP-3b, MSP-3c, and MSP-3d peptides, the numbering of the amino acid positions is done by reference to the MSP-3 protein of the 3D7 strain, which slightly differs from that of the DG 210 clone.

The MSP-3a peptide is the peptide located within the MSP-3 protein at amino acids 167 to 191 and has conformational epitopes contained in the original sequence DG210. The sequence of the MSP-3a peptide (SEQ ID No. 11) is as follows:

MSP3a: 167-YEKAKNAYQKANQAVLKAKEASSYD-191

The MSP-3b peptide is the peptide located within the MSP-3 protein at amino acids 184 to 210 and has conformational epitopes contained in the original sequence DG210. The sequence of the MSP-3b peptide (SEQ ID No. 12) is as follows:

MSP3b: 184-AKEASSYDYILGWEFGGGVPEHKKEEN-210

The MSP-3c peptide is the peptide located within the MSP-3 protein at amino acids 203 to 230 and has conformational epitopes contained in the original sequence DG210. The sequence of the MSP-3c peptide (SEQ ID No. 13) is as follows:

MSP3c: 203-PEHKKEENMLSHLYVSSKDKENISKEND-230

The MSP-3d peptide is the peptide located within the MSP-3 protein at amino acids 211 to 251 and has conformational epitopes contained in the original sequence DG210. The sequence of the MSP-3d peptide (SEQ ID No. 14) is as follows:

MSP3d: 211-MLSHLYVSSKDKENISKENDDVLDEKEEEAEETEEEELEEK-251

The immunogenic composition as described above can be administered by subcutaneous injection and at a dose of between about 3 μg to 100 μg of the long synthetic peptide comprising the epitopes contained in MSP-3a, MSP-3b, MSP-3c and MSP-3d and combinations thereof.

Another aspect of the present invention is a vaccine against malaria. This vaccine comprises a long synthetic or recombinant peptide comprising the epitopes contained within the MSP-3b peptide, the MSP-3c peptide or the MSP-3d peptide, as well as combinations of these epitopes in a pharmaceutically acceptable vehicle.

Any pharmaceutically acceptable vehicle can be used in the vaccine such as an adjuvant that enhances the immunogenicity of the long synthetic peptides. Examples of such adjuvants include alum, muramyl peptides and MONTANIDE®. MONTANIDE® are a group of oil/surfactant based adjuvants in which different surfactants are combined with either a non-metabolizable mineral oil, a metabolizable mineral oil or a mixture of the two. Other pharmaceutically acceptable vehicles include saline and the like.

The present invention also relates to a method of immunizing an individual or mammal against malaria, said method comprising administering to the mammal or individual in need of such immunization the immunogenic composition or vaccine as described above comprising a long synthetic peptide comprising the epitopes contained within the MSP-3a, MSP-3b peptide, the MSP-3c peptide or the MSP-3d peptide and combinations thereof. This vaccine or the immunogenic composition can be administered subcutaneously and at doses between of between about 3 μg to 100 μg of the long synthetic peptide comprising the epitopes contained in MSP-3a, MSP-3b, MSP-3c and MSP-3d and combinations thereof.

In yet another aspect, the present invention relates to a method for in vitro detection of a premunition state against malaria in an individual who has been immunized against malaria. As discussed above, "premunition" is a particular state of resistance contemporaneous with malaria infection and ceasing with it. The method comprising contacting a sample taken from an individual or a mammal with a native MSP-3 protein from *Plasmodium falciparum* under conditions such that there is binding between the MSP-3 protein and antibodies present in the sample. Binding to the native MSP-3 protein is indicative of a premonition state.

The conditions for this antibody/antigen binding assay are well known in the art and are described, for example, in Sambrook et al, Molecular Cloning, A Laboratory Manual, $3^{rd}$ edition (2001).

In yet another aspect, the present invention relates to a method for in vitro prognosis of the fate of a cerebral malaria patient. Cerebral malaria is a diffuse symmetric encephalopathy and is known as a severe *falciparum* malaria. Patients having this type of malaria are often in a coma and there is a mortality rate of about 20% despite treatment. Thus it was discovered that there was a significant difference in IgG3 antimalarial antibodies found in those patients that survived cerebral malaria and those who passed away after treatment with quinine.

Therefore, the method for the in vitro prognosis of the fate of a cerebral malaria patient comprises measuring the level of anti-MSP-3 IgG3 and/or IgG1 antibodies in the serum of a patient inflicted with cerebral malaria and correlating a low level of the IgG3 and/or IgG1 anti-MSP-3 antibodies with a fatal prognosis in tha absence of an adapted treatment different than just quinine. In this regard, the physician may want to change the treatment given to the patient having cerebral malaria to improve the chances of survival. Of course, the low level of the IgG3 and/or IgG1 anti-MSP-3 antibodies will be appreciated by the physician, according to known levels in the art.

Another aspect of the present invention is a method for lowering the parasitemia in a patient having malaria by administering anti-MSP-3 IgG3 or IgG1 antibodies. These antibodies can be directed for example against epitopes from the MSP-3b peptide (SEQ ID No: 12), the MSP-3c peptide (SEQ ID No: 13), or the MSP-3d peptide (SEQ ID No: 14) or against epitopes from several of these peptides. A mixture of different antibodies directed against different epitopes can be used to perform this aspect of the invention.

The invention also pertains to compositions of monoclonal or polyclonal antibodies directed against one or more polypeptides according to the invention, and to a pharmaceutical composition comprising such antibodies. These antibodies can be obtained by using standard techniques well known by the skilled artisan, and described for example in Sambrook et al, supra.

Yet another aspect of the present invention includes a kit comprising reagents for the in vitro control of a premonition state, the kit comprising a native MSP-3 protein from *Plasmodium falciparum* and reagents making possible the detection of the antigen-antibody complex produced by the immunological reaction. The kit also includes reagents making possible the detection of the antigen-antibody complex produced by the immunological reaction.

In the following examples as in all of the experiments described in the present description the immunoglobulins of human plasma are obtained by the method described by A. SABCHAREON et al, J. Trop. Med. Hyg. 1991, 45 (3): 297). The ADCI test is described above.

In the following examples the specific inhibition indices (S.I.) obtained both with sera of mice immunized with the peptide III and with immune human antibodies purified with the aid of an affinity column bearing the peptide III (procedure described in OKAZI et al.) are compared. Both the sera and the antibodies are capable of recognizing the 48 kD protein both in indirect immunofluorescence and in Western blot tests, and do so under the same conditions as previously (IgG2 of sensitive patients and IgG1 or IgG3 of protected patients). Finally, the immunopurified antibodies like the antibodies induced by injection of peptide II into the mouse tested in ADCI tests confirm that they are capable of inducing the inactivation of the parasite by the intermediary of the monocytes.

EXAMPLES

Example 1

The following Table 1 summarizes the results in support of these observations.

TABLE 1

| | Antibodies | Specific inhibition index (%) |
|---|---|---|
| Controls (+) | Pshi | 60 |
| | shi1 | 77 |
| | shi2 | 66 |
| Controls (−) | spi | 00 |
| | anti-βgal | −18 |
| Test | anti-DG210 | 45 |
| | anti-DG328 | −13 |
| | anti-DG414 | 04 |
| | anti-210B1 | 72 |
| | anti-210B2 | 80 |
| Competitions | Pshi + Acm245 | 20 |
| | Pshi + spi | 23 |

in which Pshi represents a pool of hyperimmune serum, shi1 and 2 of the hyperimmune sera of two different donors, spi and an anti-betagal, controls derived from serum after a first invasion and ans anti-betagal control, anti-DG210 are purified antibodies against peptide I, anti-210B (1) are purified human antibodies against peptide III, anti-210B (2) are the antibodies induced in the mouse and the anti-R328 and R414 are purified antibodies against peptides derived from other clones.

The specific inhibition index is that measured by the ADCI procedure.

The molecules according to the invention are hence capable of inducing the synthesis of antibodies of a class capable of cooperating with monocytes.

The proteins and peptides of the invention are not limited to those particularly described above.

The invention relates to all of the natural peptides or polypeptides obtained by genetic recombination or synthesis which exhibit the same properties of being capable of inducing immune defense mechanisms developed and characteristics of the subjects protected by malaria.

As a result of this feature, the invention relates, in particular, to epitopes of the 48 k D protein different from the polypeptides II, III and IV above. In fact, it was shown that the immunoglobulins of some individuals react with an epitope of the 48 k D protein in Western blot whereas these same immunoglobulins do not recognize the antigen expressed by the clone DG210.

The invention also relates to the polyclonal or monoclonal antibodies exhibiting the characteristic of recognizing the molecules of the invention and of cooperating with the monocytes, and capable of being used in pharmaceutical compositions to protect infected subjects by passive immunotherapy and presenting or being able to present the symptoms of the disease.

The monoclonal antibodies may be produced by the hybridoma technique in accordance with the standard procedures comprising:

- the fusion of a myeloma cell with spleen cells of an animal previously immunized with one of the antigens according to the invention,
- the culture of the hybridomas formed by the fusion of the aforementioned cells,
- and the selection of those hybridomas capable of forming monoclonal antibodies recognizing the antigen used for the immunization of the animals.

The animals selected for the immunization may be, for example, mice.

Of these monoclonal antibodies the cytophilic monoclonal antibodies will be selected advantageously, i.e., those whose Fc fragment is capable of binding of the Fc receptor of the human monocytes.

Another procedure for the production of antibodies may enable human monoclonal antibodies to be formed in vitro. To do this, B lymphocytes immortalized with, for example, the Epstein Barr virus are used. These lymphocytes may be taken from a person having been infected by *P. falciparum*. In this case, they make possible the production of monoclonal antibodies against several antigens without having recourse to in vitro stimulation by novel antigens.

Another possibility consists in fusing B lymphocytes immortalized as described above with human B lymphocytes stimulated in vitro beforehand with an antigen according to the invention against which it is desired to form monoclonal antibodies under culture conditions permitting the stimulation of the lymphocytes.

Reference will advantageously be made to the technique described by Desgranges C. et al. (1987, J. of Virological Methods, vol. 16, p281–292) for the preparation of the human monoclonal antibodies of the invention.

It is also contemplated within the framework of the invention to produce human monoclonal antibodies by genetic recombination by carrying out an in vitro transfection of the gene coding for the variable part of the antibody into vectors infecting bacteria under conditions permitting the expression of a human immunoglobulin.

Finally, the present invention relates to any type of monoclonal antibody, chimeric or hybrid, or even any fragment of polyclonal or monoclonal antibody, of the Fab or Fab'2 type, and exhibiting the same affinity characteristics of the epitopes of the 48 k D protein or the peptides I, II, III and IV below.

Preferred monoclonal antibodies according to the invention are human antibodies of class IgG1 or IgG3, or antibodies obtained in animals and having cytophilic properties in man, directed against one or more of the antigens whose sequence was described above.

The invention also relates to a procedure for monitoring the vaccination of the patient against infection with *P. falciparum*, starting from a biological sample such as blood, characterized in that it comprises:

- the placing of the biological sample likely to contain protective antibodies against *P. falciparum* in contact with a least one antigen according to the invention,
- the detection of the antigen-antibody reaction.

For carrying out this in vitro detection method the antigens according to the invention are advantageously labelled with the aid of a radioactive marker, an enzymatic or fluorescent label or even a physical type of marker.

The invention also relates to kits for the in vitro detection of the presence of antibodies directed against the antigens of the invention, characterized in that they contain:

- an antigenic composition including at least one antigen according to the invention,
- reagents necessary for carrying out the immunological reaction between the above-mentioned antigens and the antibodies possibly present in the biological sample,
- reagents making possible the detection of the antigen-antibody complex produced by the immunological reaction.

These reagents are for example labelled or capable of being recognized by a labelled reagent.

Example 2

Isolation of the Clone DG 210 a) Construction of the Library

A DNA genomic bank was constructed in the expression bacteriophage λgt11 by using the genomic DNA of the clone Tak 9-96 of *P. falciparum* (ref. clone Tak 9-96: Science 212, 137, 1981) in accordance with the protocol described in detail in the EP patent application of 9 Feb. 1987 published under the number 0343186.

Briefly, the DNA was excised by DNAase I in the presence of $Mn^{2+}$ ions, methylated by EcoRI methylase to protect the natural EcoRI sites then repaired by the DNA polymerase of the T4 bacteriophage and the DNA ligase of EcoRI. EcoRI "linkers" (synthetic oligomers) were ligated to the DNA fragments of *P. falciparum* and the artifical sites thus added were released by cutting with the enzyme EcoRI. The fragments were purified on a sucrose gradient and ligated to the DNA of the vector λgt11 suitably prepared (i.e. cut with EcoRI and dephosphorylated—sold by Promega Biotec). The DNA was encapsidated in vitro in viral particles. The bacteriophages derived from this procedure constitute a genomic DNA library.

b) Immunological Screening of the Bank

The technical details of screening are given in the text of the patent application 034186. Of a series of monoclonal antibodies (Mabs) used previously, Mab 245 (Soulier et al., Revue Française de Transfusion et Immunohématologie, Tome XXV, No 4, 1982, page 373) of class IgM, a class of antibodies incapable of cooperating with the monocytes is the only one which has proved capable of entering into competition with the polyclonal antibodies of an immune subject active in the ADCI, test, i.e., of appreciably reducing the inhibitory effect of these antibodies ADCI, suggesting that the target epitope of these antibodies capable of cooperating with the monocytes and of this Mab 245 is identical. It is this antibody which was used for the isolation of the gene by screening of a band of genomic DNA cloned in the expression vector λgt11.

A direct screening by antigen/antibody reaction with the proteins synthesized by the clones of the library proved to be unsuccessful. Since this Mab is capable of entering into competition with other antibodies for an epitope borne by the parasite protein, another method of screening was then used.

The recombinant antigens were screened by a competition test using indirect immunofluorescence. The monoclonal antibody Mab 243 in the presence of the merozoite was incubated with each of the recombinant antigens (supernatant of different clones of the genomic band) and the inhibition of the binding of the antibody to the parasite was measured by indirect immunofluorescence (technique described in H. BOUHAROUN-TAYOUN et al., 1990, J. Exp. Med. 172:1633–1641).

Six antigens proved positive, i.e. inhibitory, and were studied in detail. These six protein antigens thus selected were bound to resins in order to effect affinity purifications of the polyclonal antibodies derived from immune human sera according to the technique described by OKAZI et al. These immunoglobulins thus purified were studied. Among the latter, the one obtained by binding to the protein synthesized by the clone DG 210 recognizes in Western blot the 48 kD dimer which appears to be identical with that recognized by the cytophilic classes of IgG found in adult subjects in a state of clinical resistance to the disease and by the non-cytophilic classes of the sensitive individuals. On the other hand, it is different from the antigen MSA2, a surface antigen of the merozoite which on the same gene appears as a polypeptide of higher molecular weight (Figures). The results of Table I show that the antibodies isolated by immunoaffinity to the protein secreted by the clone DG 210 are capable of promoting in vitro the inhibitory effect on the growth off the trophozoite induced by the monocytes by the ADCI procedure.

The clone DG 210 was deposited with the CNCM on 19 Oct. 1992 under the number No. 1-1270.

Example 3

Characterization of the Protein Synthesized by the Clone DG210

The human antibodies immunoabsorbed on this protein like those produced in the mouse by immunization with the clone DG 210 show in indirect fluorescence an image in clusters designating the circumference of the merozoites within the mature intra-erythrocytic schizonts. This indication that the molecule is localized at the membrane of the merozoites was confirmed on the one hand by extraction with a non-ionic detergent, Triton X114, from purified merozoites and detection of the protein in the soluble "detergent" phase; on the other, by the action of phospholipase C of *Bacillus aureus*, this enzyme releasing the protein from a preparation of puriffied merozoites which thus indicates that the latter is anchored by a phosphatidylinositol group; finally, by revelation of the localization of the antibodies in electron microscopy with the aid of a second antibody labelled with colloidal gold: these antibodies are directed mainly against an antigen situated at the surface of the merozoites of *P. falciparum*.

These results confirm that the antigen capable of stimulating the antibody-dependent cytotoxicity mechanism (ADCI) is situated at the surface of the extracellular form of the parasite, the merozoite. In addition, the antibodies obtained by immunoaffinity on the recombinant product of the clone DG 210 have a very high inhibitory potency towards the growth of *P. falciparum* in the ADCI test whereas these same antibodies have no effect on the infection of the red cell by the merozoite. The antibody controls prepared in the same manner with other control recombinant proteins including MSA2 and RESA had no inhibitory effect either directly or in the ADCI assays (Figure). The results are found in three separate experiments involving three different isolates of antibodies. Two of these results are shown in FIG. 1.

These results are confirmed by complementary observations. The isotypic distribution of the antibodies directed against the recombinant protein derived from the clone DG 210 exhibits the following characteristics. IgG2 isotypes are found much more abundantly in the unprotected patients whereas the protein is recognized preferentially by cytophilic IgG1 and IgG3 in the blood of protected subjects. Thus, the epitopes contained in the recombinant protein of the clone DG 210 have all the desired characteristics for a protein with a vaccinating effect, namely that they might induce in vivo non-cytophilic antibodies in unprotected subjects which, on the other hand, are cytophilic in protected subjects and thus are capable of inducing the ADCI reaction in vivo.

Finally, the study of the lymphoproliferative response of 70 subjects exposed to malaria (in Senegal and Madagascar) reveals that the peptides II, III and IV define epitopes recognized by the T lymphocytes.

A strong prevalence of lymphoproliferative responses (>50% of the population study) was observed in these subjects exposed to the disease.

Example 4

Sequencing and Characterization of the Genome of the Clone DG 210

The genome of the clone DG 210 has a length of 1300 base pairs. It was possible to determine its size by using the method described by McCutchan (McCutchan et al. (1984), Science 225: 625–627). Briefly, the genome is digested by the Mung bean endonuclease, the restriction fragments are then hybridized with the DG 210 probe labelled with phosphorus 32, and revealed in autoradiography according to procedures well-known to specialists skilled in the art.

The "Northern Blot" study of these same fragments and revealed by the same radioactive probe confirms that the gene is expressed during the erythrocytic phase of the cycle of the parasite.

The analysis of the sequence of 192 base pairs of the insert was carried out by the method of Sanger et al. (PNAS, 74: 5463, 1977), called the "dideoxy-termination" method.

The invention also relates to the recombinant nucleic acids containing at least one of the polypeptide sequences I, II, III or IV or a combination of these as well as to the microorganisms, in particular *E. coli* bacteria, transformed by these recombinant nucleic acids and capable of expressing said polypeptides.

The invention relates to these nucleic acid sequences or equivalent sequences which can be synthesized and which code for the same amino acids.

It will be immediately apparent to the person skilled in the art that in these sequences some of the nucleotides may be replaced by others on account of the degeneracy of the genetic code without the encoded peptides being modified. All of these nucleotide sequences, as well as those which code for polypeptides which differ from the foregoing by one or more amino acids without their intrinsic immunogenic activity being similarly modified form part of the invention. Obviously the same holds for the nucleotide sequences which may be reconstituted and which are capable of coding for oligomers such as defined above. The monomeric motifs are directly linked end-to-end or through the intermediary of peptide sequences without effect on the immunogenic properties of the oligomers thus formed.

Finally, the invention relates to the vectors modified by these sequences, these vectors being naturally provided with regulatory and termination elements preceding and following the above-mentioned nucleic acid sequences which will permit the expression of these latter in competent cellular organisms. Among the nucleotide sequences which code for the characteristic peptides which have been defined above, mention should be made of those which are characterized by the triplet sequences which follow (SEQ IS Nos. 5–8), these sequences corresponding in particular for the first to peptide I and for the three others to peptides II, III and IV whose formulae were indicated previously

```
CAT GAA AGG GCA AAA AAT GCT TAT CAA AAA     (1)
GCA AAC CAA GCT GTT TTA AAA GCA AAA GAA
GCT TCT AGT TAT GAT TAT ATT TTA GGT TGG
GAA TTT GGA GGA GGC GTT CCA GAA CAC AAA
AAA GAA GAA AAT ATG TTA TCA CAT TTA TAT
GTT TCT TCA AAG GAT AAG GAA AAT ATA TCT
AAG GAA AAT GAG
CAT GAA AGG GCA AAA AAT GCT TAT CAA AAA     (2)
GCA AAC CAA GCT GTT TTA AAA CGA AAA GAA
GCT TCT AGT TAT GAT
GCA AAA GAA GCT TCT AGT TAT GAT TAT ATT     (3)
TTA GGT TGG GAA TTT GGA GGA GGC GTT CCA
GAA CAC AAA AAA GAA GAA AAT
CCA GAA CAC AAA AAA GAA GAA AAT ATG TTA     (4)
TCA CAT TTA TAT GTT TCT TCA AAG GAT AAG
GAA AAT ATA TCT AAG GAA AAT GAG
```

Bacteria harbouring the above-mentioned clones DG 210 were deposited with the Collection Nationale des Cultures de Microorganismes (CNCM) at the Pasteur Institute in Paris on 19 Oct. 1992 under the number 1-1270.

The object of the invention is also DNA or RNA primers utilizable, for example, in the framework of the synthesis of nucleotide sequences, possibly followed by polypeptide synthesis, according to the invention by the PCR (Polymerase Chain Reaction) procedure such as described in the American U.S. Pat. Nos. 4,683,212 and 4,683,195 and the European patent application No. 200362. A description of the procedure used here is found in the PCT patent application No. FR 91/00639, pages 28 to 30.

The peptides of the invention can also be prepared by the standard procedures used in the field of peptide synthesis. This synthesis may be carried out in homogeneous solution or on a solid phase such as described above by the procedures described in HOUBENWEYL or MERRIFIELD.

Example 5

Study of the Polymorphism of the Gene and Epitopes Defined by the Clone DG 210

A major impediment to the production of an effective vaccine is in addition to the complexity of the cycle of the parasite, its antigenic diversity and the high degree of polymorphism from one strain to another.

The conservation of the gene and defined epitopes in the clone DG 210 has been studied by several procedures in a series of isolates of plasmodiae.

By using the following nucleotides as primers SEQ ID Nos. 9–10):

or

```
GAA AGG GCA AAA AAT GCT TAT     (5)
TAA AAG GAA TCT ATA TAA AAG     (6)
```

the DNA fragments of two cultures of cultured strains of African *P. falciparum*, of 4 Thai isolates and 29 African isolates could be amplified by the PCR procedure.

The corresponding gene was present everywhere, with no apparent size polymorphism whereas a similar experiment using the same PCR procedure with primers of the MSA1 and MSA2 regions could not demonstrate this result.

Similarly, the screening of the proteins and peptides by Western blot prepared from 6 Thai or African isolates with antibodies purified using an affinity column with the peptide 210 as ligand have enabled the 48 kD dimer to be revealed in all the variants, with no change of molecular weight from one isolate to another.

Finally, 10 isolates from the Congo were studied by means of indirect immunofluorescence by the same procedure as above and were all positive, and all the parasites of each of the isolates were labelled with the antibodies purified by affinity.

Everything thus seems to point to the absence of antigenic polymorphism at least in the region of the molecule bearing the epitope B, just like the conservation of the size of this protein from one isolate to another.

These results confirm those obtained in ADCI, and more particularly in the competition tests in which the non-cytophilic antibodies obtained after an initial attack by the parasite are excellent competitors of the cytophilic antibodies of the protected adults.

In as much as the non-cytophilic antibodies obtained after the initial attack correspond to a single isolate, and the protected adults are protected against the infection of a large number of polymorphic isolates (which, furthermore, were isolated in the competition experiments), it is right to conclude that the epitopes concerned in the competition experiments are representative of non-polymorphic, conserved regions.

The polypeptides and proteins of the invention are hence characterized by a broad activity spectrum as vaccinating composition.

Example 6

Clinical Studies

The study was designed as a single site, open, randomized, dose-escalating phase I study.

The primary objectives were to evaluate the safety and tolerance of the subcutaneous (s.c.) administration of a long synthetic peptide (LSP) derived from MSP3, a *Plasmodium falciparum* merozoite surface antigen, as a potential malaria vaccine candidate, by comparing two adjuvant formulations (Alum vs MONTANIDE® 720) and four dosages of peptide (10 μg, 30 μg, 100 μg and 300 μg).

The secondary objectives were to determine the immunogenicity of LSP in the presence of adjuvant (Alum or MONTANIDE® 720), by measuring at day 0, 30, 60, 120, 150 and 360) the specific antibody and antibody subtype response to the MSP3 peptide, the antibody dependent cell inhibition (ADCI)) by evaluating antibody recognition of parasite antigen by direct immunofluorescence and by following the T-cell specific response to the MSP3 antigen (cell proliferation, cytokine production).

A total of 36 volunteers was recruited for the study and, allocated to 6 treatment groups at random in such a way that the sex and age distributions was similar in the treatment groups.

Since it was, however, difficult to recruit all 36 volunteers before the intended start of the study, the volunteers were therefore randomized to 6 treatment groups in two blocks of 18 volunteers each. The 18 volunteers in the first block were randomized to the three treatment groups in strata one and two (see Table 2 below), and the 18 volunteers in the second block to the three treatment groups in strata three and four (the strata corresponds to the days of the first injection).

TABLE 2

| Stratum | Treatment | No of volunteers |
|---|---|---|
| 1 | 10 μg LSP (MONTANIDE ® 720) | 6 |
| 2 | 30 μg LSP (Alum) | 6 |
| | 30 μg LSP (MONTANIDE ® 720) | 6 |
| 3 | 100 μg LSP (Alum) | 6 |
| | 100 μg LSP (MONTANIDE ® 720) | 6 |
| 4 | 300 μg LSP (MONTANIDE ® 720) | 6 |

There were 12 visits (inclusion visit, day 0, 2, 30, 32, 60, 120, 122, 150, 270, 360 and 540). Three injections were given (day 0, 30 and 120) and venipunctures performed 7 times (inclusion, day 0, 30, 60, 120, 150, 360).

Schedule Summary:

| | Visit Number | | | | | | | | |
|---|---|---|---|---|---|---|---|---|---|
| | V1 | V2 + 3 | V4 + 5 | V6 | V7 + 8 | V9 | V10 | V11 | V12 |
| Trial Timelines (Days,) | <30 | 0 + 2 | 30 + 32 | 60 | 120 + 122 | 150 | 270 | 360 | 540 |
| Time Windows (Days) | <30 | | ±4 | ±4 | ±4 | ±4 | ±4 | ±7 | ±14 |
| Vaccination | | x | x | | x | | | | |
| Doses | | Inj1 | Inj2 | | Inj3 | | | | |
| Biological safety | x | | X | x | | x | | x | |
| Immunology tests | | X | X | x | x | x | | x | |

Clinical Safety Tests:

Clinical safety tests were performed at the screening visit, after each blood was drawn (40 to 50 ml) during the study (months 1, 2, 3 and 6), as well as at the end of the study (month 9) and included the following tests:

RBC, hemoglobin, hematocrit, MCV, MCH, MCHC, platelets, WBC with differential counts.

Potassium, sodium, ASAT, ALAT, total bilirubin, alkaline phosphatase, λGT, creatinin, glucose.

Pregnancy test before each injection.

HIV, HCV and HBV screening test were unertaken at the inclusion visit.

Example 7

Safety Data and Amendment of the Original Protocol

The overall clinical tolerance proved to be excellent, however with a trend towards enhanced reactogenicity with MONTANIDE® as compared to alum. There were no systemic reactions, no fever or malaise and no severe adverse events. Biological tests and haematological parameters remained all along of the study, within normal ranges. However, mild, short-lived and self-resolving local erythema occurred in some of the volunteers at the site of injection, mostly when using MONTANIDE® as an adjuvant and mostly upon the second injection. This had been foreseen since it has been described with other trials relying on the use of MONTANIDE® and sometimes with alum.

Therefore, it had been decided beforehand that local reactions superior to 10 cm in diameter would lead to exclusion of the volunteers from further immunization. This criteria was revised by the clinicians who decided to exclude all reactions superior to 8 cm in diameter. The results are summarized in Table 3 below. No such reaction was seen after the first injection in any of the treated groups. After the second injection 5 occurred within the MONTANIDE® groups, 2 occurred after the third injection, one in the MONTANIDE® group and one in the alum group.

The reaction consisted of a local erythema at the site of injection and a degree of induration of the skin. It was detected on the systematic visit at 48 hours; i.e., was not a result of a complaint from the volunteer nor a consultation to the medical staff, it was not associated with pain or fever. Importantly, there was no contro-lateral reactions at the previous injection site, a phenomenon which has been described with other clinical trials relying on MONTANIDE®, particularly with the MSP-1 MONTANIDE® performed by the NIH and that performed by an Australian group in Queensland. All local reactions were spontaneously resolving within 24 hours or a maximum of 48 hours. There was no increase in size of lymph nodes at the axillary site.

Therefore, altogether, the MSP-3 immunization was better tolerated than other malarial antigens injected in volunteers with the same type of adjuvants.

| | | |
|---|---|---|
| Granuloma | ≦mo | 2 |
| Itching | | 2 |
| Unrelated event | (forearm cellulitis) | 1 |

No Systemic Adverse Reactions

Conclusions:

Good systemic tolerance

Mild, short-lived (<48 hrs) delayed type hypersensitivity reactions

Trend towards stronger reactivity with Montanide

Example 8

Amendments to the Original Protocol

In view of the existence of local reactions in the first strata of 18 volunteers and, simultaneously, of the results recorded in vitro with T-cells showing outstandingly high T-cell responses after the first immunization and standing after the second, it was considered that the doses of 10 and 30 micrograms were already optimally immunogenic and that there might be a chance to continue the dose-escalating towards the 100 and 300 micrograms initially planned. Therefore, the investigators decided to reduce those doses

TABLE 3

| | | | 1st injection | | | |
|---|---|---|---|---|---|---|
| Group | M10 | M30 | M100 | M20 | A30 | A100 |
| n | 6 | 6 | 5 | 6 | 6 | 6 |
| Induration/eryth. | 1(3 cm) | 2(3–4 cm) | 3(3–4 cm) | 2(2–3 cm) | 3(3–5 cm) | 2(3 cm) |
| Pain | 2(2/10) | — | 3(2/10) | 1(2/10) | 1(2/10) | 1(2/10) |
| Calor | — | — | 1 | — | — | 1 |
| Functional lim. | — | — | — | — | — | — |
| *Withdrawn | 0 | 0 | 0 | 0 | 0 | 0 |
| | | | **2nd injection** | | | |
| Group | M10 | M30 | M10 | M20 | A30 | A10 |
| n | 6 | 6 | 5 | 6 | 6 | 6 |
| Induration/eryth. | 1(3 cm) | 4(5–11 cm) | 4(1–8 cm) | 5(2–11 cm) | 3 (4–5 cm) | 1(2 cm) |
| Pain | 4(2–6/10) | 4(2–6/10) | 3(3/10) | 5(2–3/10) | 1(2/10) | 1(1/10) |
| Calor | 1 | 1 | 3 | 1 | — | — |
| Functional lim. | — | 1 | 1 | 1 | — | — |
| *Withdrawn | 0 | 2 | 2 | 1 | 0 | 0 |
| | | | **3rd injection** | | | |
| Group | M10 | M10 | M10 | M20 | A30 | A10 |
| n | 6 | 4 | 3 | 5 | 6 | 6 |
| Induration/eryth. | 3(3–11 cm) | 3(2–7 cm) | 1(3 cm) | 3(1–5 cm) | 5(2–11 cm) | 2(3–4 cm) |
| Pain | 4(2–4/10) | 3(2–3/10) | 1(2/10) | — | 4(2–4 cm) | 3(2/10) |
| Calor | 1 | 2 | — | 1 | 3 | — |
| Functional lim. | 1 | — | — | — | 1 | — |
| *Withdrawn | 1 | 0 | 0 | 0 | 1 | 0 |

*To designate patients who did not receive further injections, because of a local reaction > 8–10 cm in diameter and to change the protocol in the second strata and the following doses in the first strata, as follows:

The initial 10 micrograms group with MONTANIDE® remained unchanged: 3 inoculations of 10 micrograms upon each injection: i.e., M10-10-10.

The original 30 micrograms with the MONTANIDE® group received the first 2 injections of 30 micrograms and the third one was decreased to 10 micrograms: M30-30-10.

The original 100 micrograms with MONTANIDE® was revised with a first injection of 100 micrograms and following injections of 10 micrograms, i.e., M100-10-10.

The original 300 micrograms with MONTANIDE® was revised to 3 injections of 20 micrograms: i.e.,: M20-20-20.

The table of local reactions mentioned above corresponds to these new modified dosages.

Figure 2:
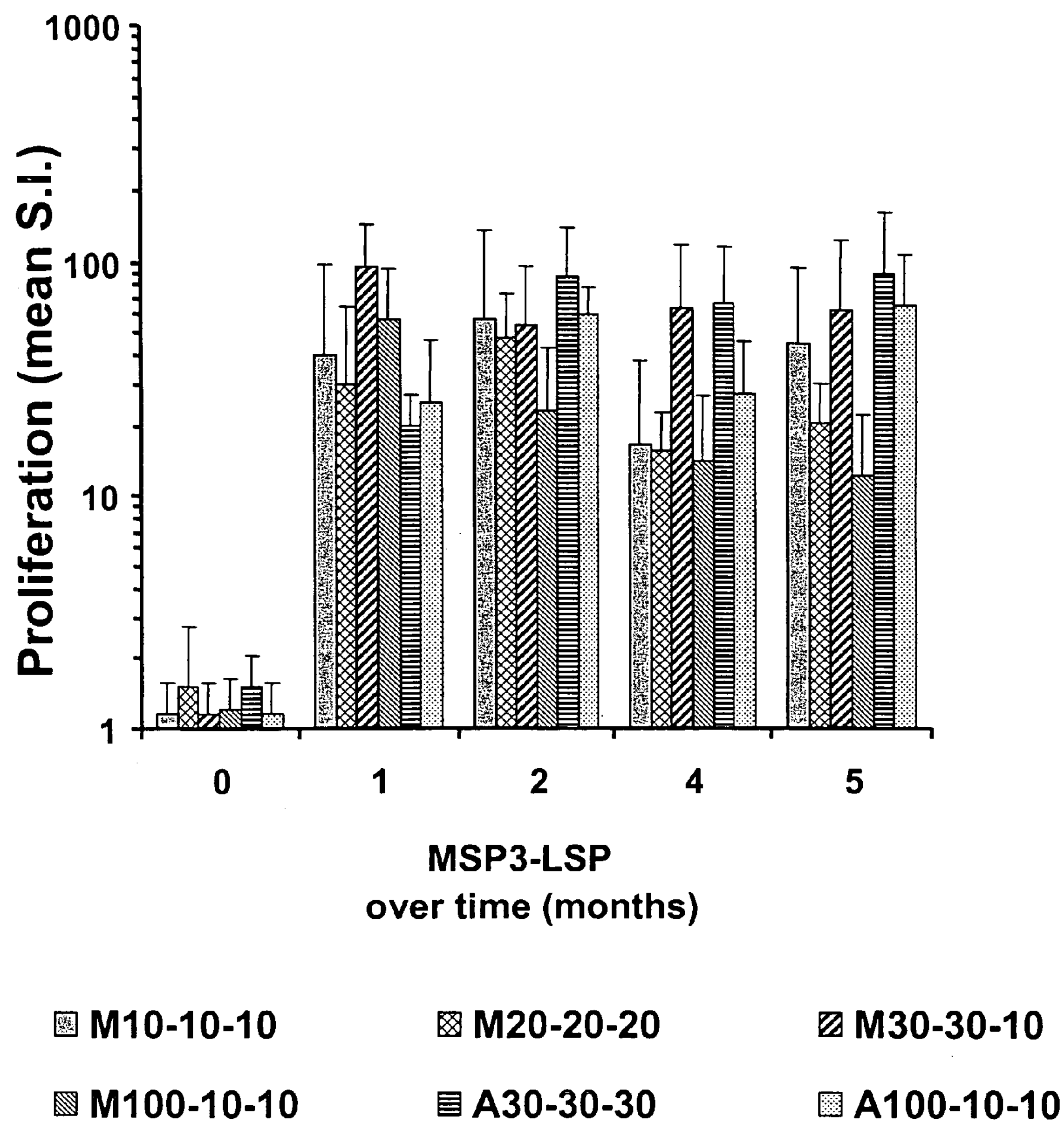
FIG. 2 is a graph illustrating the T lymphocyte responses over a period time in months using various doses of MSP3-LSP using the adjuvant Montanide (M) or Alum (A).

The results of this study are found in FIG. 2.

The follow-up was continued as planned, including visits at 6 months and at 1 year after the beginning of the immunization. No further local or general reaction was seen, no modification of hematological and biological parameters recorded.

Example 9

Immunological Data

T-Cell Responses

T-lymphocyte responses were evaluated by proliferation expressed as a stimulation index, and as Interferon-gamma secretion (the secretion of other cytokines was low). The results showed extremely high immunogenicity of the experimental vaccine with proliferative responses which were nearly as high, as the most potent stimulator (the lectin phytohaemagglutinin (PHA)) with very intense responses recorded already at the first month, i.e., after the first immunization as compared with responses obtained at month 0 before the immunization. These high responses remained overall unchanged over the follow-up, i.e., at months 2, 4 and 5, i.e., one month after the third immunization. There was some variation in the intensity of the responses depending on the protocol but, overall, all responses were high and were noticeably as high as using alum as using MONTANIDE®. The only difference with alum was that responses were somewhat lower after the first injection and increased after the second one, whereas they were maximal from the first injection when using MONTANIDE®, and remained high.

This contrasted strongly with results obtained in mice, where alum had been totally uneffective.

Similarly, IFN-gamma secretion in response to the LSP peptide were extremely high, in the range of 10 000 to 50 000 International Units, nearly as high as those induced by the potent stimulator PHA or Tetanus Toxoid (TT). They were already maximal after the first immunization and remained high over all of the immunization process with the same phenomenon of a slight increase from first to second injection with alum which was not seen with MONTANIDE®, i.e., a more progressive response obtained with alum.

Figure 3:
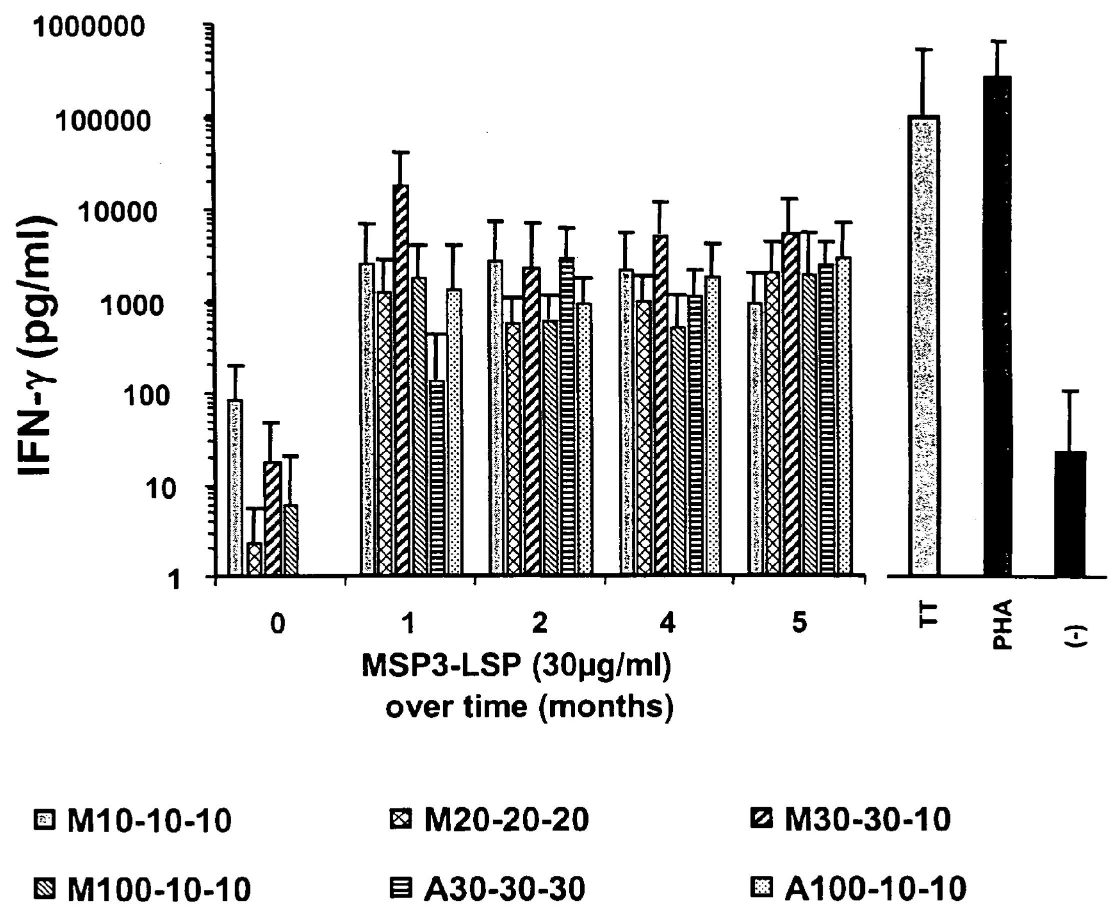
FIG. 3 is a graph illustrating IFN-gamma secretion over a period of time in months using various doses of MSP-3-LSP using the adjuvant Montanide (M) or Alum (A). A comparison of MSP-3-LSP was made with lectin phyto-haemag-glutinin (PHA) and Tetanus Toxin (TT).

The results of this study are set forth in FIG. 3.

Example 10

Antibody Responses

Figure 4A:
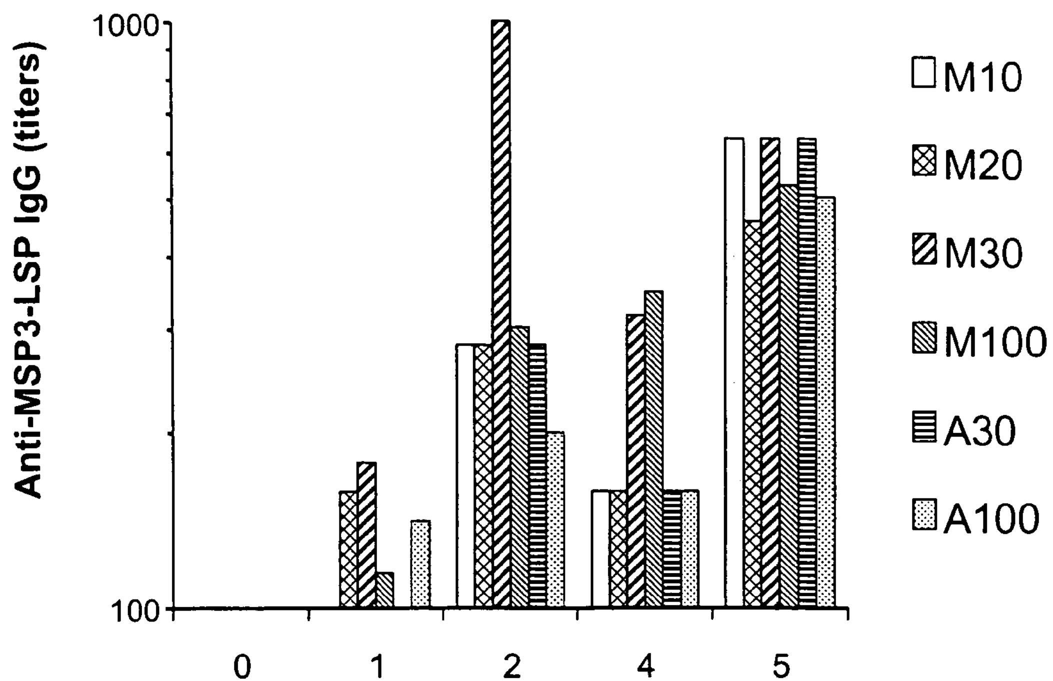
FIG. 4A is a graph illustrating the antibody response expressed in titers after the first injection of MSP-3-LSP using the adjuvant Montanide (M) or Alum (A) at various doses.
Figure 4B:
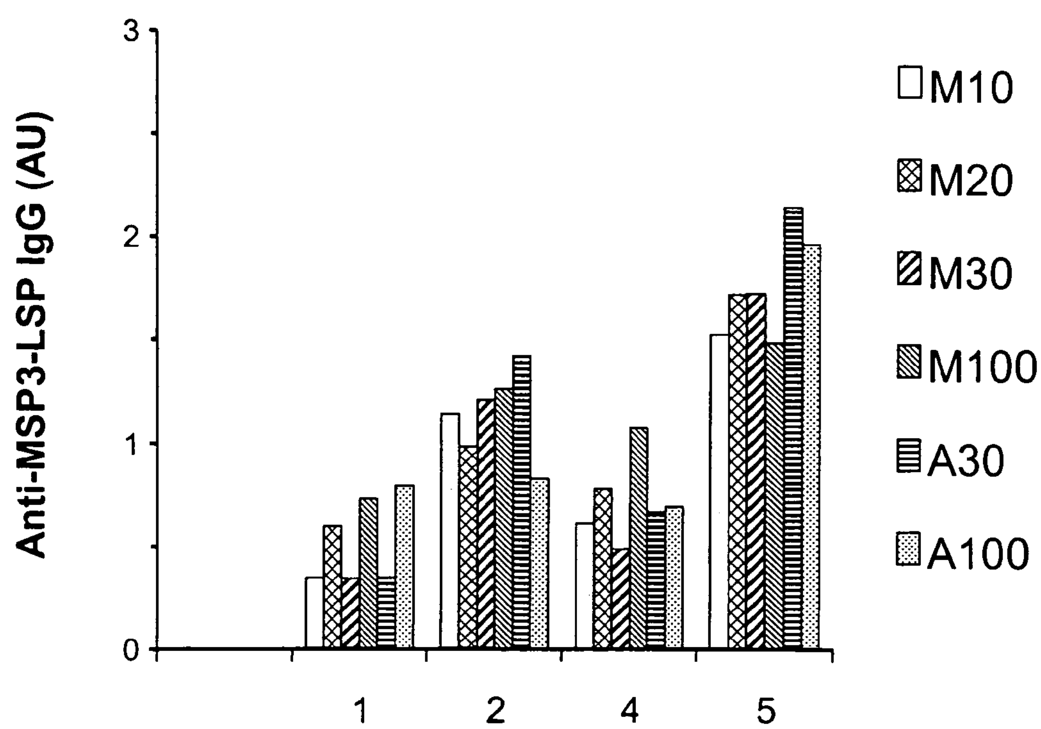
FIG. 4B is a graph illustrating the antibody response expressed in a ratio after the first injection of MSP-3-LSP using the adjuvant Montanide (M) or Alum (A) at various doses (AU=Arbitrary Unit).

Antibody responses expressed either in titers (upper graph in FIG. 4A) or in ratio (lower graph in FIG. 4B) were low after the first injection, increased markedly after the second, showed a slight decrease during the 3 month delay between the 2$^{nd}$ and 3$^{rd}$ injections and re-increased after this last boost to medium to high values. The titers were somewhat initially lower using alum as compared to Montanide but, after the third injection, all titers were within the same range with all dosages employed. The fact that antibody responses and T-cell responses remained detectable at month-4 and were boostable by the third immunization is indicative of a good memory response.

Figure 5:
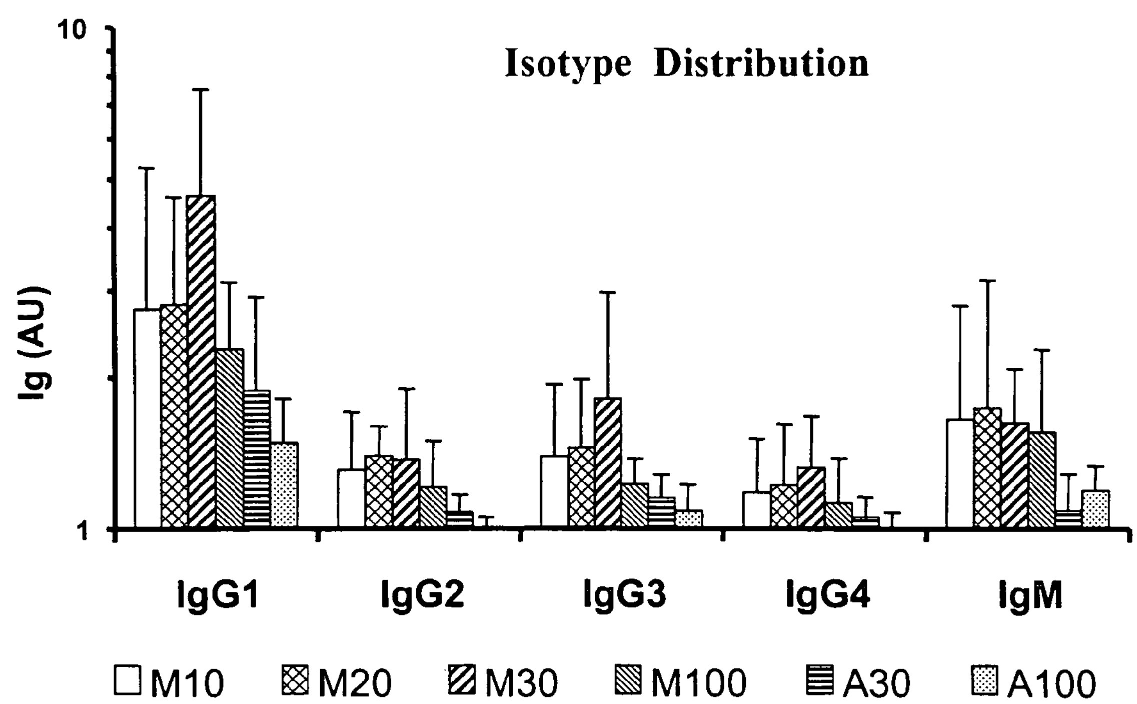
FIG. 5 is a graph illustrating the isotype distribution of the antibodies obtained after injection of MSP-3-LSP using the adjuvant Montanide (M) or Alum (A) at various doses (AU=Arbitrary Unit).

The isotype distribution of the IgG subclasses IgG1, IgG2, IgG3 and IgG4 are set forth in FIG. 5 and provided information of considerable importance: they showed that the subclasses IgG1 and IgG3 predominated over IgG2, IgG2 and IgM. This result is of considerable importance since the 2 dominating classes are the only 2 that can act in cooperation with normal monocytes to mediate the ADCI effect, since those 2 classes are cytophilic to the Fc-gamma R2 receptors on monocytes. Since field studies have shown that protection was associated not only to antibody response to MSP-3 but to the ability to produce cytophilic classes, either IgG1 or IgG3, the dominance of those 2 classes IgG1 or IgG3 is the optimal type of profile.

It should be indicated here that the IgG1 allotype in African subjects differs from that in Caucasian subjects so that there are indications that IgG1 from African subjects cannot cooperate as well as Caucasian IgG1 do with monocytes. Therefore, in African settings, it is the IgG3 subtype that correlates best with protection. Such is not the case in Caucasians where both the IgG1 allotype presented by those subject and their IgG3 can both cooperate equally well with the Fc-gamma R2 receptors on monocytes.

Hence the antibody profile was optimal as compared to the most optimistic expectations.

The study of reactivity on the native parasite proteins obtained by electrophoresis of a whole *P. falciparum* culture and transferred onto nitrocellulose probed in Western blots showed clear-cut results, each result being compared to that of a positive control, the serum of immunized mice reacting only with the 48 kDa doublet of the MSP-3. By this means, an important observation was made: although all volunteers sera post-immunization reacted to some extent with the immunizing polypeptide, the LSP and to the smaller peptides contained within, it was found that only part of the immunized volunteers could recognize and react with the native MSP-3 protein from the parasite. Altogether, 55 percent of the immunized individuals including those whose immunization schedule was discontinued, reacted with parasite native proteins (excluding those whose protocol was interrupted) led to an overall prevalence of 64% of reactions with the native protein. This result is important as it was found later in functional biological assays such as ADCI and passive transfer in SCID mice that only those individuals positive by Western blot exerted a strong ADCI effect. In contrast those with antibodies directed only to the immunizing protein and negative in Western blot did not. This demonstrated the value of this assay in prognosis terms, i.e., in terms of predicted protection if a challenge had been made.

The epitope mapping which was performed with the volunteers' sera revealed that responses were predominantly directed to epitopes denominated MSP-3-c and MSP-3-d, with little if any responses to epitope MSP-3-b. This is somewhat surprising since, under field conditions, the antibody responses were directed equally to peptides b, c and d, or predominantly to b, over c and d. this result might have to do with the construction of the LSP and the choice of the epitopes included as well as its conformation as compared to other recombinant proteins, or evidently native proteins. This result has no functional implication since results gathered in-between by epidemiological studies have shown that protection is also associated either with responses to peptide b or to peptides c and d and, in most cases, to each of them. Similarly, ADCI results have shown that antibodies specific of peptides c and d are just as much efficient as antibodies to directed to peptide b (whereas no significant effect was obtained with antibodies directed to peptides a, e and f).

Therefore although the pattern of responses on the 3 epitopes differed from that from individuals exposed to the parasite and immunized by MSP-3 presented by the parasite rather than by an artificial peptide, the results still show the induction of antibodies with demonstrated biological activity.

In total, the study of immune responses showed a very satisfactory, overall immunogenicity with extremely high T-cell responses, somewhat lower antibody responses with variations in the ability to recognize the native protein. The overall immunogenicity was much higher than that recorded in pre-clinical models employed before, i.e., in mice and in South-American primates where responses with MONTANIDE® were lower and the responses with alum were absent. This improvement in immunogenicity in humans as compared to the models is dependent on the selection of the LSP sequence based on studies made in humans and not in the models where the most relevant T-cell epitopes and B-cell epitopes have been selected by studies of the existing responses in individuals exposed to malaria under field conditions. The LSP associated 3 major T-cell epitopes in those populations and 3 major B-cell epitopes in those populations. The results lend support to the strategy by showing higher level of responses using this combination of human epitopes in humans as compared to models.

Example 11

Functional Bio-Assays

The ADCI assay and the passive transfer in SCID mice which were, in part, at the origin of the selection of the vaccine candidate, were used as one means to investigate, at an early stage, under phase-I, the actual potency and parasite killing effect of the antibodies induced in volunteers. In those conditions, results from phase-I can also provide an early indication of the results which may be gathered under phase-II with parasite challenge.

Results set forth in Table 4 below showed a clear-cut association between the ability of the antibodies induced by the LSP MSP-3 in volunteers to recognize the parasite protein in Western blots or in IFAT (immunofluoresent antibpdy test), with results from the functional bio-assays. In other words, only those volunteers having developed antibodies which could bind to the native protein on the parasite yielded a parasite killing effect. All pre-immunization samples were negative, post-immunization samples which were positive by ELISA but negative on native proteins were also negative in the bio-assays. No direct effect of the antibodies on parasite invasion (merozoite invasion into Red Blood Cells) could be seen either in pre-immunization or post-immunization samples, thereby confirming all pre-clinical data with naturally occurring antibodies.

The available data clearly show an association between the ability to recognize the native protein and the effect upon the parasite in *P. falciparum* infected-Hu RBC SCID mice. Pre-clinical samples were non effective. Similarly, no direct effect upon the parasitemia was observed in the absence of monocytes. Only a cooperation with monocytes, in agreement with previous results, was obtained with the volunteers' induced antibodies.

Thus, results obtained by ELISA, IFAT, Western blots, ADCI and passive transfer in SCID, altogether demonstrate that not only the experimental MSP-3 LSP vaccine is safe, but is immunogenic, induces the classes of IgG needed to have a biological effect and the antibodies have the ability, in cooperation to monocytes, to exert a killing effect upon *P. falciparum*.

TABLE 4

| Vol No. | Month | Western Blot | Direct Inhibition | ADCI |
|---|---|---|---|---|
| 8 | 0 | (−) | nil (−78%) | −24% |
| 8 | 5 | (++) | nil (−78%) | +76% |
| 21 | 0 | (−) | nil (−233%) | 10% |
| 21 | 5 | (++) | nil (−156%) | +84% |
| 14 | 0 | (−) | nil (−75%) | 12% |
| 14 | 5 | (++) | nil (−75%) | +82% |
| 4 | 0 | (−) | low (33%) | −20% |
| 4 | 5 | (+) | low (22%) | +97% |
| 36 | 0 | (−) | nil (−67%) | −8% |
| 36 | 5 | (−) | nil (−56%) | −16% |

CONCLUSIONS

The phase-I clinical trial conducted in 36 Swiss volunteers has provided a wealth of new information which could not be predicted by pre-clinical studies and this validates once more the value of clinical trials over that provided by models.

The Long Synthetic Peptide formulation of MSP-3 proved safe: adverse reactions were infrequent, when they occurred they were only localized and not generalized, they were self-resolving, of short duration—generally disappearing within 24 hours—, they did not induce pain and did not led the volunteers to consult: those side-effects, when they existed, were seen only on normal visits.

These results are better in terms of safety than those recorded previously using either MSP-11.19 alum or MSP-1 and MSP-2 combinations with MONTANIDE®, where severe contro-lateral effects on the previous injection sites and generalized reactions with fever were recorded.

Therefore, the LSP MSP-3 formulation can be considered safer than other vaccine candidates tested so far.

The overall immunogenicity was very good, with extremely intense immune responses, much more pronounced than those obtained in pre-clinical models, most likely reflecting the selection of relevant epitopes in the LSP by immuno-epidemiological results in exposed individuals (than a selection performed in models as is the case for many other candidates, which sometimes prove poorly immunogenic when brought into the clinic). Moreover, the low predictive value of models was demonstrated by good immunogenicity obtained when the LSP was formulated with alum whereas this adjuvant proved totally ineffective in both mice and primates.

The antibodies induced proved to be, in majority, of cytophilic classes, namely IgG1 and IgG3, the only 2 subclasses of antibodies that can bind to the Fc gamma receptors on monocytes and mediate the monocyte-dependant, antibody-mediated effect. Therefore, the Th1/Th2 balance of the immune responses induced by the vaccine preparation was optimal in terms of the type of antibodies needed and expected.

The only limitation in terms of immunogenicity, of the LSP preparation is that it induces antibodies to the immunogen itself or the peptides contained within, in ELISA studies but all volunteers did not respond by antibodies able to react with native epitopes on the parasite proteins. This may be due to the relatively short length of the LSP and was, to some extent, expected using such a short polypeptide. It should be expected that a larger number of volunteers will respond to native proteins when using larger, recombinant formulations which are planned to enter phase-I relatively soon. However, as it stands, the LSP formulation still has good safety and imumnogenicity records with a sufficiently high proportion of responders to consider its value for phase-I b trial under field conditions. This sounds particularly valuable since there are enough vials remaining of the GMP preparation which underwent phase I.a to undertake phase-I.b with the same preparation after assessing its stability.

Above all, the antibodies induced proved able to exert a specific parasite killing effect upon *P. falciparum* in the 2 predictive functional bio-assays which have been validated during all pre-clinical phases of development.

Example 12

Natural Passive Transfer of Antibodies from Mother to Newborns

During the 60 pregnancies followed up in the village of Dielmo over 10 years it was observed that the total level of antimalarial antibodies falls to lower amounts during the third trimester. The total antimalarial antibodies of each isotype was measured in the mothers before delivery, as well as isotype specific antibodies and followed up in the newborns after delivery.

In this village, where the villagers receive an average 2.5 sporozoite inocula per week, children become parasitemic by the age of 2 to 3 months. However, it turned out that this parasitemia was accompanied by clinical symptoms in some of them whereas others could stand the parasitemia without symptoms for a mean of 45 days. When comparing the levels of antibodies in the mothers and the clinical outcome in the children, it was found that IgG3 antibodies transferred from mothers to newborns were responsible for the delay of occurrence of clinical symptoms and that IgG3 anti MSP-3b antibodies strongly differentiated the 2 groups.

Example 13

Studies in Cerebral Malaria Patients

Two cohorts have been studied. In the area of Niakhar, 4,200 children were sampled during the non-transmission season and followed up during the transmission season in the dispensaries of each village. 51 experienced cerebral malaria and were all treated by quinine. Despite treatment, 9 of them died. The sera from those individuals showed significantly lower titers of anti MSP-3 antibodies as compared to the 42 cerebral malaria children who survived and as compared to a group of 100 acute uncomplicated malaria cases. A similar study was conducted in a cohort of cerebral malaria inpatients from the main hospital of Dakar, except that this time it was the serum taken upon admission which was studied. Here again, a strongly significant difference was found in IgG3 antimalarial antibodies between survivors and individuals who passed away despite adequate treatment and this difference extended to IgG3 anti MSP-3 antibodies. Those studies therefore demonstrate the prognosis role of anti MSP-3 antibodies in cerebral malaria patients (and therefore pave the way towards therapeutic antibodies).

Example 14

In Vivo Passive Transfer Experiments in *P. falciparum* Infected Scid Mice

It was recently described that *P. falciparum* growth could be obtained in immunodeficient mice grafted with human erythrocytes. This new mouse model is used for vaccine development against *falciparum* malaria determined by studying the effect of antibodies in passive transfer experiments, which effect is well established in humans. The results show that African adult immunoglobulin strongly reduces *P. falciparum* parasitaemia in similar fashion to what was reported in humans provided mice are reconstituted with human monocytes (HuMN). In contrast either immunoglobulin or HuMN alone had no direct effect upon the circulating parasitaemia in mice when added separately.

These experiments were extended to the assessment of the in vivo effect of epitope-specific antibodies. Human antibodies were affinity-purified on peptides derived either from the Ring Erythrocyte Surface Antigen (RESA) or the Merozoite Surface Antigen-3 (MSP3), their specificity and titers determined. Results showed that the inoculation of low concentrations of anti-MSP3b, but not anti-RESA antibodies, together with HuMN suppress *P. falciparum* in mice in a consistent manner. The speed of decrease of parasitaemia was as fast or faster than when using total African IgG, and as fast as that induced by chloroquine. That such a profound biological effect can be obtained using only a minor subset of the total antimalarial antibodies, those affinity purified on a single peptide from one of the numerous *falciparum* proteins, is striking. However this result is in-keeping with immuno-epidemiological observations which showed a 90% positive predictive value of the state of clinical protection of IgG3 antibodies directed to the same MSP3b peptide. The strong effect in mice of low amounts of anti-MSP3 Abs is in agreement with the relatively low levels of the same Abs in populations living in a holo-endemic area having reached clinical protection. Therefore, there is a convergence of the data obtained by 3 different means, i.e., under in vitro conditions (ADCI), in vivo conditions in mice (in Scid) or in humans (by immuno-epidemiological methods). Results demonstrate the value of the model, where antibodies with distinct specificities can be evaluated sequentially in the same animal, and also reinforce the potential of MSP3 for vaccine development.

What is claimed is:

1. An immunogenic composition comprising as an immunogen a long synthetic or recombinant peptide consisting of mixtures of a MSP-3b peptide (SEQ ID No: 12), a MSP-3c peptide (SEQ ID No: 13) and a MSP-3d peptide (SEQ ID No: 14)

* * * * *